United States Patent [19]

Liu

[11] Patent Number: 5,156,968
[45] Date of Patent: Oct. 20, 1992

[54] PURIFIED YEAST UBIQUITIN HYDROLASE

[75] Inventor: Chung-Cheng Liu, Foster City, Calif.

[73] Assignee: Genentech, Inc., South San Francisco, Calif.

[21] Appl. No.: 210,909

[22] Filed: Jun. 24, 1988

[51] Int. Cl.$^5$ .............................................. C12N 15/57
[52] U.S. Cl. .................................. 435/224; 435/212; 435/228
[58] Field of Search ............................. 435/212, 228; 530/412-417

[56] References Cited

U.S. PATENT DOCUMENTS

| | | | |
|---|---|---|---|
| 4,532,207 | 7/1985 | Brewer et al. | 435/68 |
| 4,703,004 | 10/1987 | Hopp et al. | 435/68 |
| 4,732,852 | 3/1988 | Cohen et al. | 435/68 |

FOREIGN PATENT DOCUMENTS

| | | | |
|---|---|---|---|
| 0035384 | 9/1981 | European Pat. Off. | |
| 9203493 | 4/1983 | Japan | 435/228 |
| 8802406 | 4/1988 | PCT Int'l Appl. | |
| WO8807085 | 9/1988 | PCT Int'l Appl. | |

OTHER PUBLICATIONS

Scopes, Robert K. *Protein Purification*, 1987, Springer-Verlag New York. pp. 100–107, 175–177.
Pickart and Rose, "Ubiquitin Carboxyl-terminal Hydrolase acts on Ubiquitin . . . Amides", *Journ. Biol. Chem.* 260, 13, Jul. 5, 1985.
Bachmair et al, Science 234:179–186 (1986).
Butt et al., PNAS USA, 86:2540–2544 (1989).
Hough et al., J. Biol. Chem., 261(5):2400–2406 (1986).
Mayer & Wilkinson, Biochemistry, 28:166–172 (1989).
Duerksen-Hughes et al., Biochemistry, 28:8530–8536 (1989).
Wilkinson et al., Science, 246:670–673 (1989).
Barr et al., American Chemical Society, 196th ACS National Meeting, Abstract No. 34, Sep. 25, 1988–Sep. 30, 1988.
Lund et al., J. Biol. Chem., 260(12):7609–7613 (1985).
Ozkaynak et al., EMBO J., 6(5):1429–1439 (1987).
Rechsteiner, Ubiquitin, Chpts. 2, 5 & 6 (NY: Plenum Press, (1988).
Rechsteiner, Ann. Rev. Cell Biol., 3:1–30 (1987).
Pickart & Rose, J. Biol. Chem., 261(22):10210–10217 (1986).
Kaufman et al., Gene Amplification, pp. 245–250 (Cold Spring Harbor Lab, 1982).
Pharmacia Fine Chemicals Catalogue 84, pp. 1 and 6.
Herskho et al., Proc. Natl. Acad. Sci. USA 81: 1619–1623 (1984).
Andersen et al., Biochem. 20: 1100–1104 (1981).
Kanda et al., Biochem. Biophys. Acta 870: 64–75 (1986).
Matsui et al., J. Cell Biol. 95(2); PA82 (1982).
Matsui et al., Proc. Natl. Acad. Sci. USA 79: 1535–1539 (1982).
Hershko et al., Proc. Natl. Acad. Sci. USA 77: 1783–1786 (1980).
Haas and Rose, Proc. Natl. Acad. Sci. USA 78: 6845–6848 (1981).
Kanda et al., J. Cell Biol. 99(4): PA135 (1984).
Matsui, J. Cell Biol. 105(4 part 2): 187A (1987).
Pickart and Rose, J. Biol. Chem. 260: 7903–7910 (1985).
Rose and Warms, Biochem. 22: 4234–4237 (1983).
Rose et al., Fed. Proc. 46(6): 2087 (1987).
Agell et al., Proc. Natl. Acad. Sci. USA 85: 3693–3697 (1988).
Agell et al., J. Cell Biol. 105(4 part 2) 82a (1987).
Hartley et al., Biochem. J., Index to 80: 36P (1961).

*Primary Examiner*—Jacqueline Stone
*Assistant Examiner*—Keith D. Hendricks
*Attorney, Agent, or Firm*—Janet E. Haska

[57] ABSTRACT

Ubiquitin hydrolase is provided having a purity of at least 70% homogeneity based on the weight of the total protein in the composition, which hydrolase hydrolyzes a ubiquitin-polypeptide conjugate at the amide bond linking the ubiquitin and polypeptide, thereby yielding intact polypeptide with an unconjugated, mature N-terminus. Also provided are DNA sequences encoding such ubiquitin hydrolase, as well as expression systems for its recombinant production. Processes are provided for purification of ubiquitin hydrolase from eukaryotes and for its use in recovering any desired polypeptide free from its fusion at its N-terminus with ubiquitin.

2 Claims, 16 Drawing Sheets

Fig.1a-1.

```
                                                    msei                       hphI ddeI      mnlI
     xbaI                                           TTAACAGGCA AGACTATCAC CTTAGAGGTT
  1  TCTAGAATTA TGCAAATTTT CGTCAAAACT              AATTGTCCGT TCTGATAGTG GAATCCCAA
     AGATCTTAAT ACGTTTAAAA GCAGTTTGA                LeuThrGlyL ysThrIleTh rLeuGluVal
  1            M etGlnIlePh eValLysThr bspMII
        mboII          taqI                                                                 mnlI
        hinfI          claI
 61  GAATCTTCCG ACACTATCGA TAACGTCAAA TCTAAAATTC AAGATAAAGA AGGTATCCCT
     CTTAGAAGGC TGTGATAGCT ATTGCAGTTT AGATTTTAAG TTCTATTTCT TCCATAGGGA
 18  GluSerSerA spThrIleAs pAsnValLys SerLysIleG lnAspLysLy sGlyIlePro sau3AI
        dpnI
        alwI                                                         mboII      rsaI
        mspI
        hpaII
121  CCGGATCAAC AGCGTTTGAT TTTTGCTGGT AAGCAACTAG AAGATGGTCG TACCTTGTCT
     GGCCTAGTTG TCGCAAACTA AAAACGACCA TTCGTTGATC TTCTACCAGC ATGGAACAGA
 38  ProAspGlnG lnArgLeuIl ePheAlaGly LysGlnLeuG luAspGlyAr gThrLeuSer
```

```
                                              taqI
                                              salI
                                              hincII
                                              accI   mboII
                    pleI   pleI
              pleI  hinfI  hinfI  draIII         hgaI              pleI
         fokI hinfI                                                hinfI
    181  GACTACAACA TCCAAAAGGA GTCGACTCTT CACTTGGTGT TGCGTCTCCG TGGTGGTGAC
         CTGATGTTGT AGGTTTTCCT CAGCTGAGAA GTGAACCACA ACGCAGAGGC ACCACCACTG
    58   AspTyrAsnI leGlnLysGl uSerThrLeu HisLeuVall euArgLeuAr gGlyGlyAsp hinPI
                                                                hhaI
                                      fnu4HI                    thaI
                                      haeIII                    hinPI
                                      xmaI                      hhaI
                                      eaeI                      bssHII
                                      notI   thaI               thaI
         fokI mboII                   fnu4HI   xmnI
    241  TCTTGGATGG AAGAAGTTAT CAAACTGTGC GGCCGCGAAT TAGTTCGCGC GCAGATTGCC
         AGAACCTACC TTCTTCAATA GTTTGACACG CCGGCGCTTA ATCAAGCGCG CGTCTAACGG
    78   SerTrpMetG luGluValIl eLysLeuCys GlyArgGluL euValArgAl aGlnIleAla scrFI
                hgiAI                              nlaIII
                nlaIII  bstNI                      styI   sfaNI   ddeI
         fnu4HI bsp1286                            ncoI   mboII   mnlI
    301  ATTTGCGGCA TGAGCACCTG GAGCAAAAGG TCTCTGTAGC CATGGAAGAT GCTCCTCAGA
         TAAACGCCGT ACTCGTGGAC CTCGTTTTCC AGAGACATCG GTACCTTCTA CGAGGAGTCT
    98   IleCysGlyM etSerThrTr pSerLysArg SerLeuAM*P roTrpLys fokI
    361  CACCTAGACC AGTGGCAGAA ATTGTGCCAT CCTTCATCAA CAAAGATACA GAAACCATAA
         GTGGATCTGG TCACCGTCTT TAACACGGTA GGAAGTAGTT GTTTCTATGT CTTTGGTATT
```

```
                                                                    taqI
                                                                    aluI
                                                          rsaI      sacI
                                                          nlaIV     hgiAI
                                                          kpnI      bsp1286
                                             aluI         banI      banII    ecoRI
                                             alwNI
421 ATATGATGTC AGAATTTGTT GCTAATTTGC CACAGGAGCT GAAGTTGGGT ACCGAGCTCG
    TATACTACAG TCTTAAACAA CGATTAAACG GTGTCCTCGA CTTCAACCCA TGGCTCGAGC sau3AI
    dpnI                                                            hgiAI
    xhoII                                                           bsp1286
    bglII                                        ddeI    aluI       apaLI
481 AATTCGCAAA ACCTAGCAAG AGATCTCTTG CTAGATTTTG CTGAGATGAA GCTAATTGTG
    TTAAGCGTTT TGGATCGTTC TCTAGAGAAC GATCTAAAAC GACTCTACTT CGATTAACAC sspI                       mseI                    sfaNI
541 CACATCTCGT ATAATATTCA TAATGACATT TCACTGATGC TTCTATCAGG
    GTGTAGAGCA TATTATAAGT ATTACTGTAA AGTGACTACG AAGATAGTCC mseI
                              taqI   aluI
             nlaIII   aluI    claI   hindIII                        mseI
601 TCAATTCTCA TGTTTGACAG CTTATCATCG ATAAGCTTTA ATGCGGTAGT TTATCACAGT
    AGTTAAGAGT ACAAACTGTC GAATAGTAGC TATTCGAAAT TACGCCATCA AATAGTGTCA mnlI
               nlaIV                              hinPI     fokI
               banI                               hhaI
661 TAAATTGCTA ACGCAGTCAG GCACCGTGTA TGAAATCTAA CAATGCGCTC ATCGTCATCC
    ATTTAACGAT TGCGTCAGTC CGTGGCACAT ACTTTAGATT GTTACGCGAG TAGCAGTAGG
```

```
                                                              haeIII
                                                              sau96I
                                                              scrFI
                                                      rsaI    nciI
                                                      mspI    mspI mnlI
                                                      hpaII   hpaII
                sfaNI
                fokI                                                    hinPI
        nlaIV   scrFI                                                   nheI
        banI    hphI bstNI                                              fnu4HI hhaI
                                                                        bbvI   haeII
721 TCGGCACCGT CACCCTGGAT GCTGTAGGCA TAGGCTTGGT TATGCCGGTA CTGCCGGGCC
    AGCCGTGGCA GTGGGACCTA CGACATCCGT ATCCGAACCA ATACGGCCAT GACGGCCCGG ecoRV                            sfaNI
781 TCTTGCGGGA TATCGTCCAT TCCGACAGCA TCGCCAGTCA CTATGGCGTG CTGCTAGCGC
    AGAACGCCCT ATAGCAGGTA AGGCTGTCGT AGCGGTCAGT GATACCGCAC GACGATCGCG haeIII
            hinPI                                                       eaeI
            hhaI                            hgiAI
            mstI                            bsp1286
            fspI
    sfaNI
841 TATATGCGTT GATGCAATTT CTATGCGCAC CCGTTCTCGG AGCACTGTCC GACCGCTTTG
    ATATACGCAA CTACGTTAAA GATACGCGTG GGCAAGAGCC TCGTGACAGG CTGGCGAAAC sau3AI
```

```
      fnu4HI
      fnu4HI                             nlaIV      taqI  thaI  dpnI  nlaIII
901 GCCGCCGCCC AGTCCTGCTC GCTTCGCTAC TTGGAGCCAG TATCGACTAC GCGATCATGG
    CGGCGGCGGG TCAGGACGAG CGAAGCGATG AACCTCGGTC ATAGCTGATG CGCTAGTACC
                          sau3AI
                          dpnI
                          alwI
                          xhoII
                          nlaIV
                          bamHI
                            alwI mnlI
961 CGACCACACC CGTCCTGTGG ATCC
    GCTGGTGTGG GCAGGACACC TAGG
```

Fig. 1b-1.

```
                                                                    mnlI
                                             mseI       hphI  ddeI  bspMII
   xbaI
 1 TCTAGAATTA TGCAAATTTT CGTCAAAACT TTAACAGGCA AGACTATCAC CTTAGAGGTT
   AGATCTTAAT ACGTTTAAAA GCAGTTTTGA AATTGTCCGT TCTGATAGTG GAATCTCCAA
 1   M  etGlnIlePh eValLysThr LeuThrGlyL ysThrIleTh rLeuGluVal mboII      taqI                                             mnlI
        hinfI      claI
61 GAATCTTCCG ACACTATCGA TAACGTCAAA TCTAAAATTC AAGATAAAGA AGGTATCCCT
   CTTAGAAGGC TGTGATAGCT ATTGCAGTTT AGATTTTAAG TTCTATTTCT TCCATAGGGA
18  GluSerSerA spThrIleAs pAsnValLys SerLysIleG lnAspLysGl uGlyIlePro sau3AI
      dpnI
      alwI
      mspI                                        mboII      rsaI
      hpaII
121 CCGGATCAAC AGCGTTTGAT TTTTGCTGGT AAGCAACTAG AAGATGGTCG TACCTTGTCT
    GGCCTAGTTG TCGCAAACTA AAAACGACCA TTCGTTGATC TTCTACCAGC ATGGAACAGA
38  ProAspGlnG lnArgLeuIl ePheAlaGly LysGlnLeuG luAspGlyAr gThrLeuSer
```

```
                         taqI
                         salI
                         hincII
                         accI mboII
             pleI  pleI
       fokI  hinfI hinfI            draIII              hgaI         hphI              ecoRI
181 GACTACAACA TCCAAAAGGA GTCGACTCTT CACTTGGTGT TGCGTCTCCG TGGTGGTGAA
    CTGATGTTGT AGGTTTTCCT CAGCTGAGAA GTGAACCACA ACGCAGAGGC ACCACCACTT
 58 AspTyrAsnI leGlnLysGl uSerThrLeu HisLeuValL euArgLeuAr gGlyGlyGlu taqI         fokI mboII                                    xmnI
241 TTCATCGAAG GTCGTTCTTG GATGGAAGAA GTTATCAAAC TGTGCGGTCG TGAACTGGTT
    AAGTAGCTTC CAGCAAGAAC CTACCTTCTT CAATAGTTTG ACACGCCAGC ACTTGACCAA
 78 PheIleGluG lyArgSerTr pMetGluGlu ValIleLysL euCysGlyAr gGluLeuVal mnlI
            sau3AI                                                    sau3AI
       ddeI                                       scrFI               dpnI
       hgiAI dpnI                                 bstNI               alwI
       bsp1286              accI                                      xhoII xbaI
301 CGTGCTCAGA TCGCTATCTG CGGTATGTCT ACCTGGTCTA AACGTTCTCT GTAAGATCCT
    GCACGAGTCT AGCGATAGAC GCCATACAGA TGGACCAGAT TTGCAAGAGA CATTCTAGGA
 98 ArgAlaGlnI leAlaIleCy sGlyMetSer ThrTrpSerL ysArgSerLe uOC* taqI
       salI
       hincII fnu4HI
       accI   bbvI
       pleI   pstI  aluI
       hinfI  bspMI hindIII
361 CTAGAGTCGA CCTGCAGCCC AAGCTT
    GATCTCAGCT GGACGTCGGG TTCGAA
```

```
                                                                    sau3AI
                    mseI                                             dpnI
     hincII         aflII          mseI                              bcII
     taqI
     sall
     accI
  1  GT CGACTATAAA GGTGGAAGTC CATACTTAAG AGATATTAAG GGTATTTGA TCAACAAGTA
     CA GCTGATATTT CCACCTTCAG GTATGAATTC TCTATAATTC CCATAAAACT AGTTGTTCAT nlaIV
                                                                    banI
 63  AGTAACAATC GTTATAAAAA TACAATAGCA AAAGTATGAG CGGAGAAAAT CGTGCTGTGG
     TCATTGTTAG CAATATTTT  ATGTTATCGT TTTCATACTC GCCTCTTTTA GCACGACACC
                                       MetSe     rGlyGluAsn ArgAlaValVal mseI
                                                          draI
                                                          ahaIII
                                                                         bsmI    styI
 123 TGCCGATTGA ATCAAACCCT GAAGTTTTA  CAAATTTGC ACATAAATTA GGTTTAAAAA GCATTCTTAC
     ACGGCTAACT TAGTTTGGGA CTTCAAAAAT GTTTAAAACG TGTATTTAAT CCAAATTTTT CGTAAGAATG
 10  ProIleGl   uSerAsnPro GluValPheT hrAsnPheAl aHisLysLeu GlyLeuLysAsn AlaPheLeuPro ecoRV         mseI
             taqI          aluI
 183 ATGAATGGGC GTATTTCGAT ATCTATAGCT TAACAGAGCC AGAGTTACTA
     TACTTACCCG CATAAAGCTA TAGATATCGA ATTGTCTCGG TCTCAATGAT
 30  GluTrpAl  aTyrPheAsp IleTyrSerL  euThrGluPr oGluLeuLeu haeIII      fnu4HI                                      rsaI
         haeI        bbvI                                        taqI
                                                         mnII
 243 CAAGGCCAGT GAAGGCCATT GTGCTGCTAT TTCCGATAAA CGAGGATAGA AAATCGAGTA
     GTTCCGGTCA CTTCCGGTAA CACGACGATA AAGGCTATTT GCTCCTATCT TTTAGCTCAT
 50  ArgProVa   lLysAlaIle ValLeuLeuP heProIleAs nGluAspArg LysSerSerThr
```

Fig.3b.

```
            hincII                                      mseI
303  CCAGTCAACA AATTACAAGT TCTTATGATG TTATATGGTT TAAGCAATCA GTCAAAAATG
     GGTCAGTTGT TTAATGTTCA AGAATACTAC AATATACCAA ATTCGTTAGT CAGTTTTTAC
70     SerGlnGl nIleThrSer SerTyrAspV alIleTrpPh eLysGlnSer ValLysAsnAla mspI
                                                                hpaII
                                                                scrFI
                                                                nciI
                                                           bsp1286
                                                           banII
                                                           nlaIV  nlaIV
363  CGTGCGGATT GTATGCAATT CTTCATTCTT TGAGCAATAA CCAGTCATTG TTGGAGCCCG
     GCACGCCTAA CATACGTTAA GAAGTAAGAA ACTCGTTATT GGTCAGTAAC AACCTCGGGC
90     CysGlyLe uTyrAlaIle LeuHisSerL euSerAsnAs nGlnSerLeu LeuGluProGly mseI                                        taqI
                draI                                        aluI mboII
                ahaIII
423  GCTCCGACTT GGACAATTTT TTAAAATCTC AAAGTGATAC TTCAAGCTCG AAGAATAGT
     CGAGGCTGAA CCTGTTAAAA AATTTTAGAG TTTCACTATG AAGTTCGAGC TTCTTATCCA
110    SerAspLe uAspAsnPhe LeuLysSerG lnSerAspTh rSerSerSer LysAsnArgPhe rsaI
483  TTGATGATGT TACTACCGAC CAATTCGTCT TGAATGTAAT AAAAGAGAAT GTACAAACAT
     AACTACTACA ATGATGGCTG GTTAAGCAGA ACTTACATTA TTTTCTCTTA CATGTTTGTA
130    AspAspVa lThrThrAsp GlnPheValL euAsnValIl eLysGluAsn ValGlnThrPhe
```

Fig. 3c.

```
             haeIII
             haeI
             eaeI
             balI
543  TTTCTACTGG CCAGTCAGAA GCACCAGAAG CAACTGCAGA TACTAATCTA CACTATATCA
     AAAGATGACC GGTCAGTCTT CGTGGTCTTC GTTGACGTCT ATGATTAGAT GTGATATAGT
150         SerThrGl yGlnSerGlu AlaProGluA laThrAlaAs pThrAsnLeu HisTyrIleThr
                                            pstI sau96I
                                                                nlaIV
     ndeI  mboII       mnlI                    fokI            avaII mnlI
603  CATATGTGGA AGAGAACGGA GGGATATATTG AACTGGATGG AAGGAATTTG AGCGGACCCC
     GTATACACCT TCTCTTGCCT CCCTATAAAC TTGACCTACC TTCCTTAAAC TCGCCTGGGG
170         TyrValGl uGluAsnGly GlyIlePheG luLeuAspGl yArgAsnLeu SerGlyProLeu 663  TCTATTTGGG AAAGAGTGAC CCAACTGCCA CCGATTTGAT TGAACAGGAA TTAGTTAGAG
     AGATAAACCC TTTCTCACTG GGTTGACGGT GGCTAAACTA ACTTGTCCTT AATCAATCTC
190         TyrLeuGl yLysSerAsp ProThrAlaT hrAspLeuIl eGluGlnGlu LeuValArgVal
                                                              Ub-17 Probe I
     pleI            mboII
     hinfI mnlI      mboII        mseI
723  TGAGAGTCGC CTCATATATG GAAAATGCAA ATGAAGAAGA TGTATTAAAC TTTGCTATGC
     ACTCTCAGCG GAGTATATAC CTTTTACGTT TACTTCTTCT ACATAATTTG AAACGATACG
210         ArgValAl aSerTyrMet GluAsnAlaA snGluGluAs pValLeuAsn PheAlaMetLeu
```

Fig. 3d.

```
     sau96I
     haeIII
     sau96I
     nlaIV
     ecoO
     bsp1286
     banII
     apaI
 783 TAGGATTGGG CCCTAATTGG GAATAATAAT TGTTTTATTA CTGCCTAGTC AAATATGTAT
     ATCCTAACCC GGGATTAACC CTTATTATTA ACAAAATAAT GACGGATCAG TTTATACATA
 230 GlyLeuGly ProAsnTrp GluOC* mseI
              draI
              ahaIII                  hphI
 843 TTACAGAATT CTTTTAAATA TATAATTCAC CTACTCATCA TAGCCACCGC CAAAAGAAAG
     AATGTCTTAA GAAAATTTAT ATATTAAGTG GATGAGTAGT ATCGGTGGCG GTTTTCTTTC
     ecoRI taqI
     mnlI                              taqI             claI
 903 GAAACCTCCA GTTTGTCTGG AATGTCTCGA AAAATAATCG AAATCGATGG ACACAGCGTT
     CTTTGGAGGT CAAACAGACC TTACAGAGCT TTTTATTAGC TTTAGCTACC TGTGTCGCAA sau3AI                        rsaI                  sfaNI
            dpnI                          scaI       ddeI       ddeI
     sau96I alwI
     haeIII
 963 TGCTAATAAC ACGGCCCTTT GATCCAAAGT TAGTACTTGA GAACTTAGCA TCTCAGTAGG
     ACGATTATTG TGCCGGGAAA CTAGGTTTCA ATCATGAACT CTTGAATCGT AGAGTCATCC sfaNI
     sspI           hinfI             fau4HI
1023 ATAAATATTA TCAAAGCATC TCTGCGAATC AAATCT  C  CATAAACAC CAGTAT~300→BamHI
     TATTTATAAT AGTTTCGTAG AGACGCTTAG TTTAGA  G           GTCATA    GTATTGTG
```

PURIFIED YEAST UBIQUITIN HYDROLASE

BACKGROUND OF THE INVENTION

This invention relates to the purification of ubiquitin hydrolase having enzymatic activity in cleaving ubiquitin-protein conjugates. This invention also relates to a process for preparing the ubiquitin hydrolase using recombinant methods and a process for using same to isolate polypeptides from fusions thereof with ubiquitin.

The polypeptide known as ubiquitin is highly conserved, has a molecular weight of 8,565, and contains 76 amino acid residues. It is encoded by genes that contain varying numbers of the protein sequence repeated without any stop codons between them or with other proteins.

Ubiquitin was first purified during studies of peptides of the thymus. Radioimmunoassays for the peptide revealed that it was found widely in plant, animal, and yeast. Goldstein et al., *Proc. Natl. Acad. Sci. U.S.A* 72: 11-15 (1975). The sequence of amino acids 1-74 of thymus ubiquitin was determined by Schlesinger et al., *Biochemistry*, 14: 2214-2218 (1975). revealing an $NH_2$-terminal methionine and an arginine at position 74. The sequence was confirmed by Low et al., *J. Biol. Chem.*, 254: 987-995 (1979). This form was later shown to be a degraded form of ubiquitin and is not active in its biological function. The active form is the 76 amino acid form. Wilinson and Audhya, *J. Biol. Chem.*, 256: 9235-9241 (1981).

It has been found that ubiquitin is involved in the energy-dependent degradation of intracellular proteins. Evidence exists that in eukaryotes, covalent conjugation of ubiquitin to the proteins is essential for their selective degradation, Finley et al., *Trends Biochem. Sci.*, 10: 343 (1985) and Finley et al., *Cell*, 37: 43 (1984).

Isopeptidases have been identified that are unique for eukaryotes. They are found to cleave in vitro an amide bond formed between a ubiquitin Gly-COOH terminal and epsilon-$NH_2$ group of lysine on other polypeptides. For example, an isopeptidase was identified that cleaves the linkage between ubiquitin and lysozyme to yield free lysozyme. Hershko et al., *Proc. Natl. Acad. Sci. U.S.A.*, 81: 1619-1623 (1984). An isopeptidase was also detected in reticulocyte extracts that cleaves ubiquitin-histone 2A conjugates, with the release of undegraded histone. Andersen et al , *Biochemistry*, 20 1100-1104 (1981), Kanda et al., *Biochim. Biophys. Acta*, 870: 964-75 (1986), Matsui et al., *J. Cell Biol.*, 95: (2) PA82 (1982), and Matsui et al., *Proc. Natl. Acad. Sci. U.S.A.*, 79: 1535-1539 (1982). See also Hershko et al., *Proc. Natl. Acad. Sci.* U.S.A., 77: 1783-1786 (1980) and Haas and Rose. *Proc. Natl Acad. Sci.* U.S.A., 78: 6845-6848 (1981).

Isopeptidase was purified 175-fold from calf thymus by ion-exchange chromatography, gel filtration, and affinity chromatography on whole histone and histone H2A Sepharose. Kanda et al., *J. Cell Biol.*, 99: (4), PA135 (1984) This purified isopeptidase was found to be specific to the epsilon-(glycyl)lysine linkage in structural chromatin protein A24.

When the isopeptidase was purified, it was found to exist in growing Chinese hamster cells as two major forms having molecular weight 250,000 and 34,000, but was found to be present in human erythrocytes and calf thymus only in the 250.000 molecular weight form. These two forms of enzyme were found to be distinct from one another, in that the degradation of the large form did not result in the appearance of the smaller form. Matsui, *J. Cell Biol.*, 105: (4 Part 2), 187A (1987). The author suggests that the large form is a stable constitutive enzyme and that the small form with a rapid turnover rate is linked to the metabolic pathway of growth-related ubiquitin-protein conjugates. Isopeptidase activity of 30 kDa on silver stained SDS-PAGE (called carboxyl-terminal hydrolase) was also identified in human red blood cells. Pickart and Rose, *J. Biol. Chem.*, 260: 7903-7910 (1985). This enzyme was formerly called ubiquitin carboxyl-terminal esterase because it was found to hydrolyze ubiquitin esters of small thiols. Rose and Warms, *Biochemistry*, 22: 4234-4237 (1983).

An activity of ubiquitin-specific processing protease is reported in WO 88/02406 published Apr. 7, 1988, in the context of designing or modifying protein structure at the protein or genetic level to produce specified amino termini based on introducing the use of artificial ubiquitin-protein fusions.

Ubiquitin aldehyde was found to form strong complexes with most hydrolases, e.g., the major ubiquitin-protein hydrolase of greater than 200 KDa, a small 30 KDa cationic hydrolase, and the major hydrolase of 30 KDa that acts on small molecule conjugates of ubiquitin. Rose et al., *Fed Proc* 46: (6), 2087 (1987). It was concluded that ubiquitin hydrolases, in addition to being important in rescuing ubiquitin from traps with small nucleophiles, are necessary for recycling ubiquitin from protein conjugates that are only slowly degraded.

Another discovery regarding cleavage of ubiquitin-protein conjugates revealed that when a chimeric gene encoding a ubiquitin-beta-galactosidase fusion protein was expressed in yeast, ubiquitin was cleaved from the fusion protein, yielding a deubiquitinated beta-galactosidase. This cleavage was found to take place regardless of the nature of the amino acid residue of beta-gal at the ubiquitin-beta-gal junction, with one exception. Bachmair et al., *Science*, 234: 179-186 (1986). It was also found that different residues could be exposed at the amino-termini of the otherwise identical beta-gal proteins. These authors suggested that the same protease, as of then uncharacterized biochemically, was responsible both for the conversion of polyubiquitin into mature ubiquitin and for the deubiquitination of the nascent ubiquitin-beta-gal protein.

Different investigators detected a proteolytic activity that converted the polyubiquitin to ubiquitin when a coupled in vitro transcription/translation system was employed. Agell et al., *J. Cell Biol.*, 105: (4 pt 2), 82a (1987) and Agell et al., *Proc. Natl. Acad. Sci.*, U.S.A., 85: 3693-3697 (1988). The polyubiquitin processing activity was partially inhibited by ubiquitin aldehyde, a known inhibitor of ubiquitin hydrolase. A purified preparation of this proteolytic activity was found to be inactive, with further purification of the putative protease then reported to be in progress.

Regarding the purification of substances using an irreversible step such as cleavage, it was reported that fragments of proteins can be separated by charge or size in one dimension and then a reagent used to alter the protein fragments irreversibly for visualization in a second dimension. The objective of this work was to obtain amino acid sequence from the protein. Hartley et al., *Biochem. J.*, 80: 36 (1961).

In addition, it is known to recover and purify a protein from its fusion product with an "identification"

peptide. EP 150,126 published Jul. 31, 1985. In this process a hybrid polypeptide is synthesized with the identification peptide fused to a desired functional protein at the C-terminus of the identification peptide. The linking portion of the identification peptide is cleaved at a specific amino acid residue adjacent to the functional protein by using a sequence-specific proteolytic enzyme or chemical agent. The hybrid polypeptide is purified by affinity chromatography using an immobilized ligand specific to the antigenic portion of the identification peptide. The protein is then cleaved from the isolated hybrid polypeptide with an appropriate proteolytic agent to release the mature functional protein.

The major problem associated with cleaving fusion proteins produced by recombinant means has been the lack of specific cleaving agents to remove the fusion protein moiety from the product protein in an exact and consistent manner. Chemical agents such as cyanogen bromide or hydroxyamine, or specific proteases such as Factor Xa or collagenase, that are used generally to achieve cleavage typically are only commercially practical in a limited number of protein fusion cleavages.

For example, if the specific amino acid that is required for the cleavage of a fusion protein (such as methionine for cyanogen bromide) is present internally in the amino acid sequence of the desired protein product, the product will be clipped internally as well as cleaved from the fused polypeptide. For this reason and other reasons, the cleaving agents are generally specific only for one protein product. In addition, the cleavage itself may leave extra amino acid residues on the product protein. Furthermore, almost all of the cleaving agents require extra recovery steps to purify the more complex mixture that is generated after cleavage.

Accordingly, it is an object of the present invention to provide a ubiquitin hydrolase that is purified to a sufficient degree that it can be sequenced.

It is another object to provide quantities of ubiquitin hydrolase useful for commercial purposes by using recombinant means to produce the polypeptide, free of source proteins.

It is another object to provide a method for producing and purifying mature polypeptides, the method being characterized by removing the fusion protein moiety from the product moiety specifically and efficiently, by reducing the number and complexity of fusion recovery steps, and by obtaining precise and reproducible cleavage of the product free of extra unwanted terminal amino acid residues.

These and other objects will be obvious to those of ordinary skill in the art.

SUMMARY OF THE INVENTION

In one aspect of the invention herein, these objects are achieved by a composition comprising ubiquitin hydrolase in a purity of at least 70% homogeneity based on the weight of the total protein in the composition, which hydrolase hydrolyzes a ubiquitin-polypeptide conjugate at the amide bond linking the ubiquitin and polypeptide, thereby yielding intact polypeptide with an unconjugated, mature N-terminus.

In another aspect, the invention herein provides a process comprising:

(a) homogenizing a eukaryotic cell fermentation paste and recovering the portion from the homogenate containing ubiquirin-hydrolase activity;

(b) salting out from the recovered hydrolase-containing portion of step (a) a precipitate containing ubiquitin-hydrolase activity;

(c) contacting a solution of the precipitate with an ion exchange resin and recovering the ubiquitin-hydrolase-active fraction;

(d) contacting a ubiquitin hydrolase-active fraction with a hydrophobic affinity resin and recovering the ubiquitin-hydrolase active fraction adsorbed to the resin;

(e) contacting a ubiquitin hydrolase-active fraction with an adsorption chromatography resin and recovering the ubiquitin-hydrolase-active fraction adsorbed to the resin; and (f) contacting a ubiquitin-hydrolase-active fraction with an ion exchange resin and recovering the hydrolase-active fraction.

In yet another aspect, the invention provides an isolated nucleic acid sequence comprising a sequence that encodes ubiquitin hydrolase or fragments or variants thereof, an expression vector comprising this nucleic acid sequence operably linked to control sequences recognized by a host transformed by the vector, and host cells transformed by such a vector. The nucleic acid is preferably DNA, but can also be RNA or an RNA vector (retrovirus).

In a more specific aspect, the invention provides an isolated DNA sequence comprising a sequence that hybridizes under stringent conditions to the DNA sequence of FIG. 3 and that contains at least about ten nucleotides. Preferably the DNA sequence contains at least about twenty nucleotides.

In yet another embodiment, the invention provides an isolated DNA sequence comprising a DNA sequence encoding an enzyme having an amino acid sequence sufficiently duplicative of that of ubiquitin hydrolase to allow it to hydrolyze a ubiquitin-polypeptide conjugate at the amide bond linking the ubiquitin and polypeptide, thereby yielding intact polypeptide with an unconjugated, mature N-terminus. The invention also provides for expression vectors containing such DNA sequence operably linked to appropriate control sequences, and hosts such as *E. coli* transformed with such vectors.

In a further aspect, the invention sets forth a method comprising:

(a) providing a ubiquitin-polypeptide conjugate in a composition comprising contaminant products of recombinant host cell culture, wherein the polypeptide is conjugated to the C-terminus of the ubiquitin and wherein the polypeptide contains any amino acid at its N-terminus;

(b) contacting the composition with a reagent having specific affinity for ubiquitin so that the conjugate is adsorbed on the reagent, separating the reagent and its adsorbed conjugate from the rest of the composition, and recovering the conjugate from the reagent;

(c) contacting the recovered conjugate with ubiquitin hydrolase whereby the conjugate is hydrolyzed to ubiquitin and mature polypeptide and the ubiquitin hydrolase is immobilized; and (d) contacting the material obtained from step (c) with a reagent having specific affinity for ubiquitin so that any residual conjugate and free ubiquitin are adsorbed on the reagent, and recovering the polypeptide free from the reagent and the materials adsorbed thereon.

In still another aspect, the invention is directed to a method comprising:

(a) providing a ubiquitin-polypeptide conjugate in a composition comprising contaminant products of recombinant host cell culture, wherein the polypeptide is conjugated to the C-terminus of the ubiquitin and wherein the polypeptide contains any amino acid at its N-terminus;

(b) contacting the composition with a reagent having specific affinity for ubiquitin so that the conjugate is adsorbed on the reagent and separating the reagent and its adsorbed conjugate from the rest of the composition;

(d) contacting the reagent on which is adsorbed the conjugate with ubiquitin hydrolase;

(e) separating the hydrolase and polypeptide from the reagent; and (f) separating the polypeptide from the hydrolase.

In further aspects, the invention provides an enzyme composition comprising the ubiquitin hydrolase of this invention in a buffer and a kit comprising ubiquitin hydrolase as one component and immobilized anti-ubiquitin antibody as a second component.

The present invention makes it possible to produce ubiquitin hydrolase or derivatives thereof by recombinant techniques, as well as to provide products and methods related to such production In addition, this invention enables a simplified and effective method for recovering mature proteins and polypeptides from their fusion with another protein. Further, the invention allows variant polypeptides and proteins to be expressed without concern about secretion or cleavage in undesired positions.

BRIEF DESCRIPTION OF THE DRAWINGS

FIGS. 1a-1 through 1a-5 depict the sequence of a synthetic gene encoding a ubiquitin fusion polypeptide wherein the polypeptide is the naturally occurring human (H2) relaxin B chain. FIGS. 1b-1 through 1b-2 depict the sequence of a synthetic gene encoding a ubiquitin fusion polypeptide wherein the polypeptide is the human (H2) relaxin B chain of 32 amino acids (missing the N-terminal amino acid) linked at its N-terminus to a hexapeptide. The hexapeptide is in turn linked at its N-terminus to the C-terminus of ubiquitin. The six amino acids do not code for any known sequence. FIGS. 1c-1 through 1c-2 depict the construction of pT7-12, an intermediate plasmid providing the phi 10 promoter recognized by T7 polymerase (PT7), and the construction of the vectors containing ubiquitin fusion polypeptides used in the assay for the ubiquitin hydrolase activity.

FIG. 2 is a schematic depiction of the ubiquitin hydrolase assay.

FIGS. 3a through 3d depicts the nucleotide and predicted amino acid sequence of yeast ubiquitin hydrolase. Predicted amino acids of the protein are shown below the DNA sequence and are numbered from the first residue of the proposed N-terminus of the protein sequence. The figure also indicates the amino acid sequence of the polypeptide used to derive Probe 1 for screening a yeast genomic library to obtain a clone encoding ubiquitin hydrolase.

FIG. 4 depicts the orientation of the BamHI-SalI fragment in M13mp18 and M13mp19 for sequencing the gene coding for the ubiquitin hydrolase.

DETAILED DESCRIPTION OF THE PREFERRED EMBODIMENTS

A. Definitions

Figures 1, 1C:
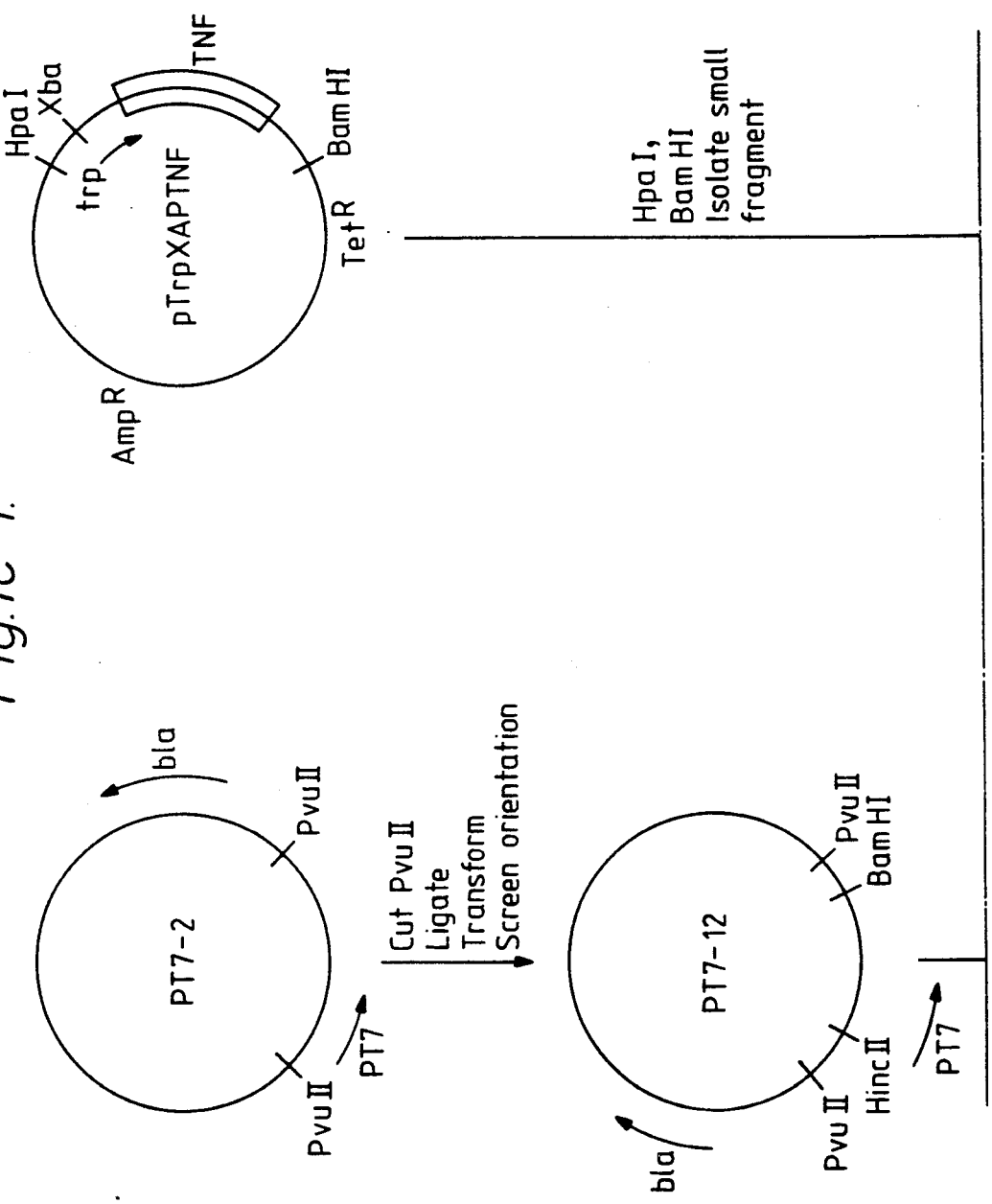

The term "ubiquitin hydrolase" as used herein refers to an enzyme having the amino acid sequence of FIG. 3 and derivatives and amino acid sequence variants thereof that possess ubiquitin hydrolase biological activity. Biological activity is one or both of (a) the capability to hydrolyze a ubiquitin-polypeptide conjugate at the amide bond linking the ubiquitin and polypeptide, thereby yielding intact polypeptide with an unconjugated, mature N-terminus, or (b) the ability to cross-react with an antibody that binds to the FIG. 3 polypeptide. The full-length ubiquitin hydrolase has a molecular weight of about 29,000 daltons on a reducing SDS-PAGE gel. The amino acid sequence from the cloned gene revealed the molecular weight as 26,000 daltons. Generally, the enzyme is from eukaryotes.

Derivatives and amino acid sequence variants are defined as molecules in which the amino acid sequence, glycosylation, or other feature of native ubiquitin hydrolase, has been modified covalently or noncovalently. Amino acid sequence variants include not only alleles of the FIG. 3 sequence, but also predetermined mutations thereof. Generally, amino acid sequence variables have an amino acid sequence with at least about 80% homology, and more typically at least about 90% homology, to that of the native ubiquitin hydrolase of FIG. 3. Henceforth, the term "ubiquitin hydrolase" shall mean either the native sequence or variant form unless otherwise appropriate.

Thus, included within the scope of the present invention is ubiquitin hydrolase having the amino acid sequence as set forth in FIG. 3, analogous ubiquitin hydrolase proteins from other microbial, vertebrate, or invertebrate eukaryotic species such as insect, human, bovine, equine, porcine, ovine, canine, murine, feline ubiquitin hydrolase, and the like, and biologically active amino acid sequence variants of these ubiquitin hydrolases, including alleles and in vitro-generated covalent derivatives of ubiquitin hydrolase proteins that demonstrate the enzyme's activity.

The term "polypeptide" refers to a product with more than one peptide bond, including a dipeptide, tripeptide, and proteins of any size, or a mutant or fragment thereof.

The expression "at least 70% homogeneity" refers to the weight of ubiquitin hydrolase in total protein, as determined by a comparative visual inspection of a silver-stained SDS-PAGE gel for relative intensities of the bands.

The term "buffer" refers to a buffer that is characterized by its ability to stabilize the enzyme herein at a suitable pH range, of generally around 3 to 10, more preferably 4 to 8.

B. Modes of Carrying Out the Invention

1. Purification of Ubiquitin Hydrolase

The steps involved in purifying the ubiquitin hydrolase of this invention are enumerated below. This method is useful for purifying ubiquitin hydrolase from recombinant or non-recombinant cells.

Eukaryotic cells, preferably yeast such as Saccharomyces cerevisiae or another yeast strain, are fermented, as by using standard conditions known in the art, and a fermentation paste is obtained. The paste is homogenized and the portion from the homogenate containing ubiquitin-hydrolase activity is recovered, preferably by centrifugation. The activity may be assayed as described in the examples.

A precipitate containing ubiquitin-hydrolase activity is salted out from the recovered hydrolase-containing portion. Preferably the salting out is done using ammonium sulfate fractionation, but any salt suitable for this purpose may be employed.

A solution of the precipitate is contacted with an ion exchange resin and the ubiquitin-hydrolase-active fraction is recovered. Preferably the ion-exchange resin is a DEAE chromatography column and the fraction is adsorbed to the column and recovered from the column.

The ubiquitin hydrolase-active fraction is contacted with a hydrophobic affinity resin, such as a phenyl, octyl, or cetyl sepharose chromatographic column, and the ubiquitin-hydrolase-active fraction adsorbed to the resin is obtained and recovered. The fraction recovered from this step is preferably dialyzed against a buffer before the next step is performed.

The ubiquitin-hydrolase-active fraction is contacted with an adsorption chromatography resin, such as a hydroxyapatite or silica column, and the ubiquitin-hydrolase-active fraction adsorbed to the resin is recovered.

The fraction recovered from this step is preferably dialyzed against a buffer before the next step is performed. Most preferably, the adsorption chromatography is done by hydroxylapatite column chromatography and the active fraction is adsorbed to the column and recovered therefrom.

The ubiquitin-hydrolase-active fraction is again contacted with an ion-exchange resin, such as a DEAE chromatography column and the hydrolase-active fraction is adsorbed to the column and recovered therefrom.

The ubiquitin hydrolase from the active fraction ubiquitin hydrolase is then generally isolated in a purity of at least 70% by the weight of the total protein. Liquid chromatography may be employed in this isolation procedure.

2. Modifications of Ubiquitin Hydrolase

Derivatives and amino acid sequence variants of ubiquitin hydrolase are useful for their enzymatic activity, as is set forth elsewhere herein, as well as for their ability to bind to anti-ubiquitin hydrolase antibodies. The derivatives and variants possessing the latter characteristic are useful in purifying antibodies or, when labeled, as reagents in immunoassays for ubiquitin hydrolase, whether or not such derivatives and variants retain their enzymatic activity.

7 a. Covalent modification

Covalent modifications of the ubiquitin hydrolase molecule are included within the scope of this invention. Variant ubiquitin hydrolase fragments having up to about 100–150 residues may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with o-haloacetates (and corresponding amines), such as chloroacetic acid or chloroacetamide to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents among them phenylglyoxal 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N—C—N—R') such as 1-cyclohexyl3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the ubiquitin hydrolase to a water-insoluble support matrix or surface for use in the method for cleaving ubiquitin fusion polypeptides to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including dissuccinimidyl esters such as 3,3'-dithiobis(succinimidylpropionate), and bifunctional maleimides such as bis-N-maleimido-1,8-octane. Derivatizing agents such as methyl. 3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016;

4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the o-amino groups of lysine, arginine and histidine side chains (T. E. Creighton, *Proteins: Structure and Molecular Properties.* W. H. Freeman & Co., San Francisco, pp. 79-86 [1983]), acetylation of the N-terminal amine, and, in some instances, amidation of the C-terminal carboxyl group.

Amino acid sequence variants of ubiquitin hydrolase can also be prepared by mutations in the DNA. Such variants include, for example, deletions from, or insertions or substitutions of, residues within the amino acid sequence shown in FIG. 3. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the ubiquitin hydrolase, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed ubiquitin hydrolase variants screened for the optimal combination of desired activity. Techniques for making substitution mutations at predetermined sites in DNA having a known sequence are well known, for example, M13 primer mutagenesis.

Amino acid sequence deletions generally range from about 1 to 30 residues, more preferably 1 to 10 residues, and typically are contiguous.

Amino acid sequence insertions include amino, and/or carboxyl-terminal fusions of from one residue to polypeptides of essentially unrestricted length, as well as intrasequence insertions of single or multiple amino acid residues. Intrasequence insertions (i.e., insertions within the mature ubiquitin hydrolase sequence) may range generally from about 1 to 10 residues, more preferably 1 to 5. An example of a terminal insertion includes a fusion of a signal sequence, whether heterologous or homologous to the host cell, to the N-terminus of the ubiquitin hydrolase to facilitate the secretion of mature ubiquitin hydrolase from recombinant hosts.

The third group of variants are those in which at least one amino acid residue in the ubiquitin hydrolase molecule, and preferably only one, has been revved and a different residue inserted in its place. Such substitutions preferably are made in accordance with the following Table 1 when it is desired to modulate finely the characteristics of the ubiquitin hydrolase molecule.

TABLE I

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in ubiquitin hydrolase properties will be those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine or proline residue is substituted for (or by) any other residue; (d) a residue having an electropositive side chain, e.g., lysyl, arginyl, or histidyl, is substituted for (or by) an electronegative residue. e.g., glutamyl or aspartyl; or (e) a residue having a bulky side chain, e.g , phenylalanine, is substituted for (or by) one not having such a side chain. e.g., glycine.

Most deletions and insertions, and substitutions in particular, are not expected to produce radical changes in the characteristics of the ubiquitin hydrolase molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native ubiquitin hydrolase-encoding nucleic acid, expression of the variant nucleic acid in recombinant cell culture, and, optionally, purification from the cell culture, for example, by immunoaffinity adsorption on a rabbit polyclonal anti-ubiquitin hydrolase column (to absorb the variant by at least one remaining immune epitope).

The activity of the cell lysate or purified ubiquitin hydrolase variant is then screened in a suitable screening assay for the desired characteristic. For example, a change in the immunological character of the ubiquitin hydrolase, such as affinity for a given antibody, is measured by a competitive-type immunoassay. Changes in immunomodulator activity are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

b. Site-Specific Mutagenesis

Preparation of ubiquitin hydrolase variants in accordance herewith is preferably achieved by site-specific mutagenesis of DNA that encodes an earlier prepared variant or a nonvariant version of the protein. Site-specific mutagenesis allows the production of ubiquitin hydrolase variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., DNA. 2: 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA,* Editor A. Walton, Elsevier, Amsterdam (1981), the disclosure of which is incorporated herein by reference. These phage are readily commercially available and their use is generally wall known to those skilled in the art. Alternatively, plasmid vectors that contain a single-stranded phage origin of replication (Veira et al., *Meth. Enzymol.,* 153: 3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA).* 75: 5765 (1978). This primer is then annealed with the single-stranded protein sequence-containing vector, and subjected to DNA-polymerizing enzymes such as *E. coli* polymerase I Klenow fragment to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

3. Recombinant Expression

DNA encoding ubiquitin hydrolase may be obtained from yeast or other sources than yeast by (a) obtaining a cDNA library from cell lines expressing ubiquitin hydrolase mRNA of the particular species, (b) conducting hybridization analysis with labeled DNA encoding yeast ubiquitin hydrolase or fragments thereof (usually greater than 100 base pairs in length) to detect clones in the cDNA library containing homologous sequences, and (c) analyzing the clones by restriction enzyme analysis and nucleic acid sequencing to identify full-length clones. If full-length clones are not present in the library, then appropriate fragments may be recovered from the various clones using the nucleic acid sequence information disclosed herein for the first time and ligated at restriction sites common to the clones to assemble a full-length clone encoding ubiquitin hydrolase. Alternatively, genomic libraries will provide the desired DNA.

Ubiquitin hydrolase may be made by any technique, including both synthetic and recombinant methods. Likewise, an isolated DNA is understood herein to mean chemically synthesized DNA, cDNA, chromosomal, or extrachromosomal DNA with or without the 3' and/or 5' flanking regions. Preferably, the ubiquitin hydrolase herein is made by synthesis in recombinant cell culture. For such synthesis, it is first necessary to secure nucleic acid that encodes ubiquitin hydrolase. The sequence of the yeast DNA encoding ubiquitin hydrolase that was ultimately determined is shown in FIG. 3. Once this DNA has been identified, using hybridization of several synthetic probes, the DNA isolated from the library is ligated into a replicable vector for further cloning or for expression. DNA that is capable of hybridizing to the DNA of FIG. 3 under stringent conditions is useful as probes for identifying DNA encoding ubiquitin hydrolase from yeast or other eukaryotes Stringent conditions are defined further below.

In one example of a recombinant expression system ubiquitin hydrolase is expressed in prokaryotes by transforming with an expression vector comprising DNA encoding ubiquitin hydrolase. It is preferable to transform host cells capable of accomplishing such processing so as to obtain the hydrolase in the culture medium or periplasm of the host cell.

a. Useful Host Cells and Vectors

The vectors and methods disclosed herein are suitable for use in host cells over a wide range of prokaryotic and eukaryotic organisms.

In general, of course, prokaryotes are preferred for the initial cloning of DNA sequences and constructing the vectors useful in the invention. For example, *E. coli* K12 strain 294 (ATCC No. 31,446) is particularly useful. Other microbial strains that may be used include *E. coli* strains such as *E. coli* B, and *E. coli* X1776 (ATCC No. 31,537). These examples are, of course, intended to be illustrative rather than limiting.

Prokaryotes may also be used for expression. The aforementioned strains, as well as *E. coli* W3110 (F-, lambda-, prototrophic, ATCC No. 273325). bacilli such as *Bacillus subtilis,* and other enterobacteriaceae such as *Salmonella typhimurium* or *Serratia marcesans,* and various pseudomonas species may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene.* 2: 95 (1977)). PBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang et al., *Nature*, 375: 615 (1978); Itakura et al., *Science* 198: 1056 (1977); Goeddel et al., *Nature*, 281: 544 (1979)) and a tryptophan (trp) promoter system (Goeddel et al., *Nucleic Acids Res.*, 8: 4057 (1980); EPO Appl. Publ No. 0036,776). While these are the most commonly used, other microbial promoters have been discovered and utilized, and details concerning their nucleotide sequences have been published, enabling a skilled worker to ligate them functionally with plasmid vectors (see. e g., Siebenlist et al., *Cell*, 20: 269 (1980)).

In addition to prokaryotes, eukaryotic microbes, such as yeast cultures, may also be used. *Saccharomyces cerevisiae* or common baker's yeast, is the most commonly used among eukaryotic microorganisms, although a number of other strains are commonly available. For expression in *Saccharomyces*, the plasmid YRp7. for example (Stinchcomb et al., *Nature*, 282: 39 (1979); Kingsman et al., *Gene*. 7: 141 (1979); Tschemper et al., *Gene*, 10: 157 (1980)) is commonly used. This plasmid already contains the trol gene that provides a selection marker for a mutant strain of yeast lacking the ability to grow in tryptophan, for example, ATCC No. 44.076 or PEP4.1 (Jones, *Genetics*, 85: 12 (1977)). The presence of the trol lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J Biol. Chem.*, 255: 2073 (1980)) or other glycolytic enzymes (Hess et al . *J. Adv. Enzyme Reg.*, 7: 149 (1968); Holland et al., *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al., *Nature*, 273: 113 (1978)). Smaller or larger SV40 fragments may also be used, provided there is included the approximately 250-bp sequence extending from the HindIII site toward the BzlI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno VSV, BPV) source, or may be provided by the host cell chromosomal replication mechanism. If the vector is integrated into the host cell chromosome, the latter is often sufficient.

In selecting a preferred host cell for transfection by the vectors of the invention that comprise DNA sequences encoding both variant t-PA and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (USA) 77: 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line. CHO-K1 (ATCC No. CCL 61).

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate, thus permitting control of expression by control of the methotrexate (MTX) concentration.

b. Typical Methodology Employable

If cells without formidable cell membrane barriers are used as host cells, transfection is carried out by the calcium phosphate precipitation method as described by Graham and Van der Eb, *Virology*, 52: 546 (1978). However, other methods for introducing DNA into cells such as by nuclear injection or by protoplast fusion may also be used.

If prokaryotic cells or cells that contain substantial cell wall constructions are used, the preferred method of transfection is calcium treatment using calcium as described by Cohen et al., *Proc. Natl. Acad. Sci.* (USA) 69: 2110 (1972).

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of Polymerase I (Klenow). phenol-chloroform extracted, and ethanol precipitated.

Size separation of the cleaved fragments is performed using 6 percent polyacrylamide gel described by Goeddel et al., *Nucleic Acids Res.*, 8: 4057 (1980).

For ligation, approximately equimolar amounts of the desired components, suitably end tailored to provide correct matching, are treated with about 10 units T4 DNA ligase per 0.5 μg DNA. (When cleaved vectors are used as components, it may be useful to prevent religation of the cleaved vector by pretreatment with bacterial alkaline phosphatase.)

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared, analyzed by restriction mapping and/or DNA sequencing by the method of Messing et al., *Nucleic Acids Res.*, 9: 309 (1981) or by the method of Maxam et al., *Methods of Enzymology*, 65: 499 (1980).

After introduction of the DNA into the mammalian cell host and selection in medium for stable transfectants, amplification of DHFR-protein-coding sequences is effected by growing host cell cultures in the presence of approximately 20,000–500,000 PM concentrations of methotrexate, a competitive inhibitor of DHFR activity. The effective range of concentration is highly dependent, of course, upon the nature of the DHFR gene, protein and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

4. Process for Cleaving Fusion Polypeptides

The ubiquitin hydrolase herein is particularly useful in a process for readily processing a fusion polypeptide between ubiquitin and any polypeptide product desired. Ubiquitin fusion polypeptides are expressed generally by a chimeric gene construct comprising a ubiquitin gene ligated at its 3' end to the 5' end of a gene coding for the desired polypeptide. The ubiquitin gene is obtained from a natural source and cloned into an appropriate vector, as described in WO 88/02406. supra the disclosure of which is incorporated herein by reference, or it is synthesized chemically, using, e.g., the method described by Ecker et al., *J. Biol. Chem.*, 262:3524–3527 (1987) and Ecker et al., *J. Biol. Chem.*, 262: 14213–14221 (1987). the disclosures of which are incorporated by reference. The fusion in turn optionally contains an N-terminal signal sequence to facilitate secretion of the fusion polypeptide.

The codon for the N-terminal amino acid of the desired polypeptide is located directly adjacent to the 3' end of the ubiquitin gene or is separated by any number of nucleotide triplets (typically one, two or three triplets) that need not encode any particular sequence but which keep the gene encoding the desired polypeptide in the correct reading frame.

The desired polypeptide may be any polypeptide, including, but not limited to, mammalian polypeptides such as, e.g., relaxin A-chain, relaxin B-chain, prorelaxin, and mouse gonadotropin associated peptide, and microbial proteins. Preferably the polypeptide is a polypeptide heterologous to the host cell in which it is expressed, and is a human polypeptide. In addition, one or more predetermined amino acid residues on the polypeptide may be substituted, inserted, or deleted, without adversely affecting the expression and/or ubiquitin hydrolase processing of the fusion.

The fusion is produced in a composition comprising contaminant products of recombinant cell culture and then cleaved so as to recover the desired polypeptide product. The polypeptide is conjugated to the C-terminus of the ubiquitin and contains any amino acid at its N-terminus. The host cell culture containing the fusion is grown in culture medium appropriate to the host and harvested by a method dependent on whether the fusion is secreted. In general, the cells are lysed and centrifuged to spin out the cellular debris and recover the fusion protein in the supernatant. The supernatant or secreted fusion material recovered from the periplasm, e.g., by osmotic shock, or from the extracellular medium is then contacted with a reagent having specific affinity for ubiquitin so that the conjugate is adsorbed on the reagent. This reagent may be any reagent, such as a cellular protein that interacts with the ubiquitin or an anti-ubiquitin antibody, preferably a monoclonal antibody. Most preferably, the separation takes place on an affinity chromatography column to which a monoclonal antibody against ubiquitin is bound.

In the next step, the reagent having specific affinity for ubiquitin and its adsorbed conjugate is separated from the rest of the host cell culture, and the conjugate is recovered from the reagent. If the adsorbed conjugate is on an affinity column, the conjugate adsorbed to the antibody is recovered by elution from the column using a pH gradient of 4–5.

In the following step, the recovered conjugate is contacted with ubiquitin hydrolase, whereby the conjugate is hydrolyzed to ubiquitin and mature polypeptide and the hydrolase is immobilized. This may be accomplished by passing the eluted conjugate through a column to which the ubiquitin hydrolase is bound. Alternatively, the conjugate is contacted with ubiquitin hydrolase and then an antibody against the hydrolase that is immobilized is used to separate the hydrolase from the conjugate.

The recovered material is then contacted with a reagent having specific affinity for ubiquitin so that any residual conjugate and free ubiquitin are adsorbed on the reagent, and the polypeptide is recovered free from the reagent and the materials adsorbed thereon. Again, this reagent may be a monoclonal antibody against ubiquitin, which may be bound to an affinity column.

For the success of this process, the host cell preferably produces no endogenous ubiquitin hydrolase that will interfere with the recovery process. This can be achieved either by using a prokaryotic host, which in general produces no ubiquitin hydrolase, or by employing deletion or transposon mutagenesis to rid the host cell, i.e., a eukaryotic host cell, of the gene that codes for the endogenous ubiquitin hydrolase. It may also be desirable to select host cells deficient in endogenous proteases that might degrade the fusion polypeptide if it is produced intracellularly, e.g., in a prokaryotic host.

In another method for recovering the cleaved polypeptide, after the host cell culture producing the conjugate is harvested as described above, the culture is contacted with the reagent having specific affinity for ubiquitin so that the conjugate is adsorbed on the reagent (the reagent being defined as described above). The reagent and its adsorbed conjugate are separated from the rest of the culture. Then the reagent on which is adsorbed the conjugate is contacted with the ubiquitin hydrolase. The hydrolase and polypeptide are separated from the reagent, and, in a final step, the polypeptide is separated from the hydrolase. The same preferred embodiments mentioned for the first process also apply to this process.

5. Antibodies to Ubiquitin

Antibodies to ubiquitin generally are raised in animals by multiple subcutaneous or intraperitoneal injections of ubiquitin and an adjuvant. It may be useful to conjugate the ubiquitin to a protein that is immunogenic in the species to be immunized, e g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$ or $R^1N=C=NR$. Also, aggregating agents such as alum may be used to enhance the immune response.

Animals are immunized against the immunogenic conjugates or derivatives by combining 1 mg or 1 μg of conjugate (for rabbits or mice, respectively) with three volumes of Freund's complete adjuvant and injecting the solution intradermally at multiple sites. One month later the animals are boosted with 1/5 to 1/10 the original amount of conjugate in Freund's complete adjuvant by subcutaneous injection at multiple sites. Seven to 14 days later animals are bled and the serum is assayed for anti-ubiquitin titer. Animals are boosted until the titer plateaus. Preferably, the animal is boosted with the conjugate of the same ubiquitin polypeptide, but conjugated to a different protein and/or through a different crosslinking agent.

Monoclonal antibodies are prepared by recovering spleen cells from immunized animals and immortalizing the cells in conventional fashion, e.g., by fusion with myeloma cells or by Epstein-Barr virus transformation and screening for clones expressing the desired antibody. Monoclonal antibodies to ubiquitin are described, for example, in Smith and Fried. *Fed. Proc.*, 46(6): 2087 (1987), and polyclonal antisera are described by Redman et al., *J. Biol. Chem.*, 263: 4926–4931 (1988).

6. Kit Components

A composition of the ubiquitin hydrolase herein may be formulated in a buffer for stability purposes. The buffer can be composed of inorganic or organic salts and includes, for example citrate, phosphate, or Tris buffer, depending on the pH desired.

Further, the composition of the ubiquitin hydrolase may be one component of a kit, which also contains an immobilized antibody to ubiquitin hydrolase as the second component. The antibody may be immobilized as described above regarding modifications to ubiquitin. Such a kit can be used for performing cleavage of fusion proteins containing ubiquitin conjugated to the desired protein.

In order to simplify the examples and claims certain frequently occurring methods will be referenced by shorthand phrases.

"Transfection" refers to the taking up of an expression vector by a host cell whether or not any coding sequences are in fact expressed. Numerous methods of transfection are known to the ordinarily skilled artisan, for example, $CaPO_4$ and electroporation. If prokaryotic cells or cells that contain substantial cell wall constructions are used, the preferred method of transfection is calcium treatment using calcium chloride as described by Cohen, F. N. et al., *Proc. Natl. Acad. Sci.* (USA) 69: 2110 (1972). Successful transfection is generally recognized when any indication of the operation of this vector occurs within the host cell.

"Transformation" means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described by Cohen, S. N. *Proc Natl. Acad. Sci.* (USA), 69: 2110 (1972), is generally used for prokaryotes or other cells that contain substantial cell-wall barriers. For mammalian cells without such cell walls, the calcium phosphate precipitation method of Graham, F. and van der Eb, A., *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al., *J. Bact.* 130: 946 (1977) and Hsiao, C. L., et al., *Proc. Natl. Acad. Sci.* (USA) 76: 3829 (1979). However, other methods for introducing DNA into cells such as by nuclear injection or by protoplast fusion may also be used.

As used herein, the expression "hybridize under stringent conditions" to describe certain DNA sequences encompassed within the scope of this invention refers to hybridizing under conditions of low ionic strength and high temperature for washing, for example, 0.15 M NaCl/0.015 M sodium citrate/0.1% $NaDodSO_4$ at 50° C., or alternatively the presence of denaturing agents such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate, at 42° C. for hybridization.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Operably linked" refers to juxtaposition such that the normal function of the components can be performed. Thus, a coding sequence "operably linked" to control sequences refers to a oonfiguration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences which are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the site for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al , 1982, *Molecular Cloning* pp. 133–134).

"Recovery" or "isolation" of a given fragment of DNA from a restriction digest means separation of the digest on polyacrylamide or agarose gel by electrophoresis identification of the fragment of interest by comparison of its mobility versus that of marker DNA fragments of known molecular weight, removal of the gel section containing the desired fragment, and separation of the gel from DNA. This procedure is known generally. For example, see R Lawn et al., 1981, *Nucleic Acids Res.* 9: 6103–6114, and D. Goeddel et al., 1980, *Nucleic Acids Res.* 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided. Southern analysis shall mean separation of digests on 1 percent agarose, denaturation and transfer to nitrocellulose by the method of E. Southern, 1975, *J. Mol. Biol.* 98: 503–517, and hybridization as described by T. Maniatis et al., 1978, *Cell* 15: 687–701.

"Transformation" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., 1970, *J. Mol. Biol.* 53: 154.

"Ligation" refers to the process of forming phosphodiester bonds between two double-stranded nucleic acid fragments (T. Maniatis et al., supra, p. 146). Unless otherwise provided, ligation may be accomplished using known buffers and conditions with 10 units of T4

DNA ligase ("ligase") per 0.5 μg of approximately equimolar amounts of the DNA fragments to be ligated.

"Preparation" of DNA from transformants means isolating plasmid DNA from microbial culture. Unless otherwise provided the alkaline/SDS method of Maniatis et al., Id., p. 90, may be used.

"Oligonucleotides" are short-length single- or double stranded polydeoxynucleotides that are chemically synthesized by known methods (such as phosphotriester, phosphite, or phosphoramidite chemistry, using solid-phase techniques such as described in EP Pat. Pub. No. 266,032 published May 4, 1988, or via deoxynucleoside H-phosphonate intermediates as described by Froehler et al., Nucl. Acids Res., 14: 5399-5407 (1986)). They are then purified on polyacrylamide gels.

The following examples are intended to illustrate the best mode now known for practicing the invention, but the invention is not to be considered limited thereto.

All literature citations herein are expressly incorporated by reference.

EXAMPLE I

I. Protein Assay

A. PREPARATION OF 35-S LABELED PROTEIN SUBSTRATE FOR UBIQUITIN HYDROLASE

This labeling procedure was carried out in vivo in an *E. coli* strain that contains an integrated bacteriophage T7 RNA polymerase gene and a plasmid containing a gene for a protein substrate to be labeled. The expression of the protein substrate gene was under the control of T7 RNA polymerase promoter, whose sequences were located 5' to the protein substrate gene on the plasmid. The expression of T7 RNA polymerase gene was under the control of the lac promoter of *E. coli.*

DNA fragments encoding yeast ubiquitin fusion polypeptides were synthesized chemically on a DNA synthesizer using the method of Froehler et al., supra. The synthetic ubiquitin fusion gene for human (H2) relaxin B chain of 33 amino acids obtained from natural sources is shown in FIG. 1a. The synthetic ubiquitin fusion gene for human (H2) relaxin B chain of 32 amino acids (missing the N-terminal amino acid of relaxin B, but adding six amino acids at the junction of ubiquitin and the relaxin chain) is shown in FIG. 1b. The synthesis of the gene of ubiquitin with a cysteine dipeptide at its 3' end was performed using the same ubiquitin gene. The synthesis of the gene of ubiquitin fused at its 3' end to human (H2) relaxin B chain with 29 amino acids (truncated at its 3' end by four amino acids) was accomplished in the same way, as was the synthesis of the gene of ubiquitin fused at its 3' end to human relaxin A chain with 25 amino acids. The nucleotide sequence of relaxin A chain can be found in European Pat. Pub. No. 112,149 published Jun. 27, 1984. To the ends of the synthesized ubiquitin fusion polypeptide genes were added a XbaI and BamHI site.

It can be seen from FIGS. 1a and 1b that the ubiquitin gene has a convenient unique DraIII site at nucleotides 211-216 that can be used to attach various proteins, if the protein to be attached is linked to the remainder of the nucleotides needed to construct the ubiquitin 3' end and has a DraIII site inserted.

FIG. 1c shows the construction of the vectors encoding the ubiquitin protein substrates with the various synthetic relaxin chains. First, plasmid pT7.2 was obtained from United States Biochemical Corporation. The plasmid DNA was cleaved with PvuI and religated. The DNA was used to transform competent bacteria and clones were screened for inversion of the PvuI fragment. One such inverted clone was called pT7-12. The purpose of this construction was to prevent high-level expression of the beta-lactamase gene, which otherwise would be transcribed under the control of the phi 10 promoter. pT7-12 was cleaved with HincII and BamHI and the large fragment isolated.

A second plasmid, pTrpXAPTNF, was prepared from pBR322 and contains the tumor necrosis factor (TNF)-encoding gene under the control of the trp promoter. The construction of this gene is described fully in EP Pub. No. 168,214, published Jan. 15, 1986, the disclosure of which is incorporated herein by reference. This plasmid was cleaved with HoaI and BamHI and the small fragment was isolated. This small fragment was then ligated to the large fragment from PT7-12, to form the plasmid pT7-12TNF, which contains the TNF-encoding gene and the Xba site within the trp leader ribosome binding site.

The plasmid pT7-12TNF was cleaved with Xba and BamHI and the large fragment isolated. This large fragment was then ligated to one of the synthetic DNA fragments of ubiquitin-relaxin or ubiquitin-cys-cys, to yield plasmids wherein the synthetic fragments are under the control of the PT7 promoter. These plasmids are designated pT7-cys, pT7-RB32, pT7-RB29, pT7-RBnat, and PT7-RA, for the cys-cys dipeptide, relaxin B 32 synthetic chain, relaxin B 29 synthetic chain, relaxin B 33 natural chain, and relaxin A 24 chain, respectively.

*E. coli* K5772 bacteria (deposited in the American Type Culture Collection under accession number 53,635) were made competent and transformed with pT7-RB32, pT7-RB29, pT7-RBnat, pT7-RA, and pT7-cys, separately. Cells were selected for resistance to carbenicillin.

The *E. coli* transformant was grown overnight at 37° C. to saturation in 5 ml of M9 minimal media supplemented with 50 μg/ml each of all amino acids except for cysteine and methionine. (Because of the fast interconversion between cysteine and methionine in vivo, labeling done in the absence of exogenously added methionine will result in the labeling of the methionine residue in the protein. Because of the interconversion, labeling done in the presence of exogenously added methionine will result in the almost nondetectable incorporation of S35 into the methionine residue.) The presence of glucose ensured catabolite repression of the lac promoter controlling T7 RNA polymerase transcription. Fifty μg/ml of carbenicillin was also included to maintain the plasmid.

The overnight culture was diluted 50-fold into 1 ml of M9 minimal media supplemented with 10 μg/ml each of amino acids except for cysteine and methionine plus 50 μg/ml of carbenicillin.

After three hours of shaking at 37° C., isopropylthio-βD-galactoside (IPTG) was added to the culture to give a final concentration of 1 mM to induce the synthesis of T7 RNA polymerase. After another 30 minutes, 20 mg/ml Rifampicin was added to give a final concentration of 200 μg/ml to inhibit host RNA polymerase activity. Another 30 minutes later, 35S cysteine (600 Ci/mmole) was added to the culture at the ratio of 0.25 mCi/ml culture to label the proteins or the cys-cys dipeptide.

The labeling was done at 37° C. for ten minutes and was stopped by quenching the culture with cysteine at final concentration of 50 μg/ml and the bacterial pellet was collected by centrifugation.

The lysis of the cell can be carried out differently depending on the purpose of the cell lysate to be used. The following procedure was used to prepare lysate that contains all soluble *E. coli* proteins (it contains the labeled protein if it is soluble) in a solution that is compatible with almost all enzymatic processes to be examined under aqueous conditions without further treatment. The ratio of various reagents to culture volume was based on a 1-ml labeling culture.

To the collected bacterial pellet, 80 μl of a solution containing 50 mM Tris-Cl (pH 8), 25% (w/v) sucrose was added to resuspend the cells. This step as well as all the following steps were carried out at room temperature.

To the cell suspension. 20 μl of 5 mg/ml lysozyme freshly dissolved in 0.25 M Tris-Cl (pH 8.0) was added and incubated for five minutes. Forty μl of 0.25 M EDTA (pH 8) was then added to the suspension.

After another five minutes of incubation, cells were lysed by adding 60 μl of the lytic mix containing 50 mM Tris-Cl (pH 8), 50 mM EDTA (pH 8), 0.2% (v/v) NP40. It required between 5 and 10 minutes to obtain complete cell lysis. The lysate was clarified by centrifugation and was ready to be used or could be kept at −20° C. for a long period of time.

B. Ubiquitin Hydrolase Assays

1. Fusion protein cleavage assay

Figures 1, 1C, 2:
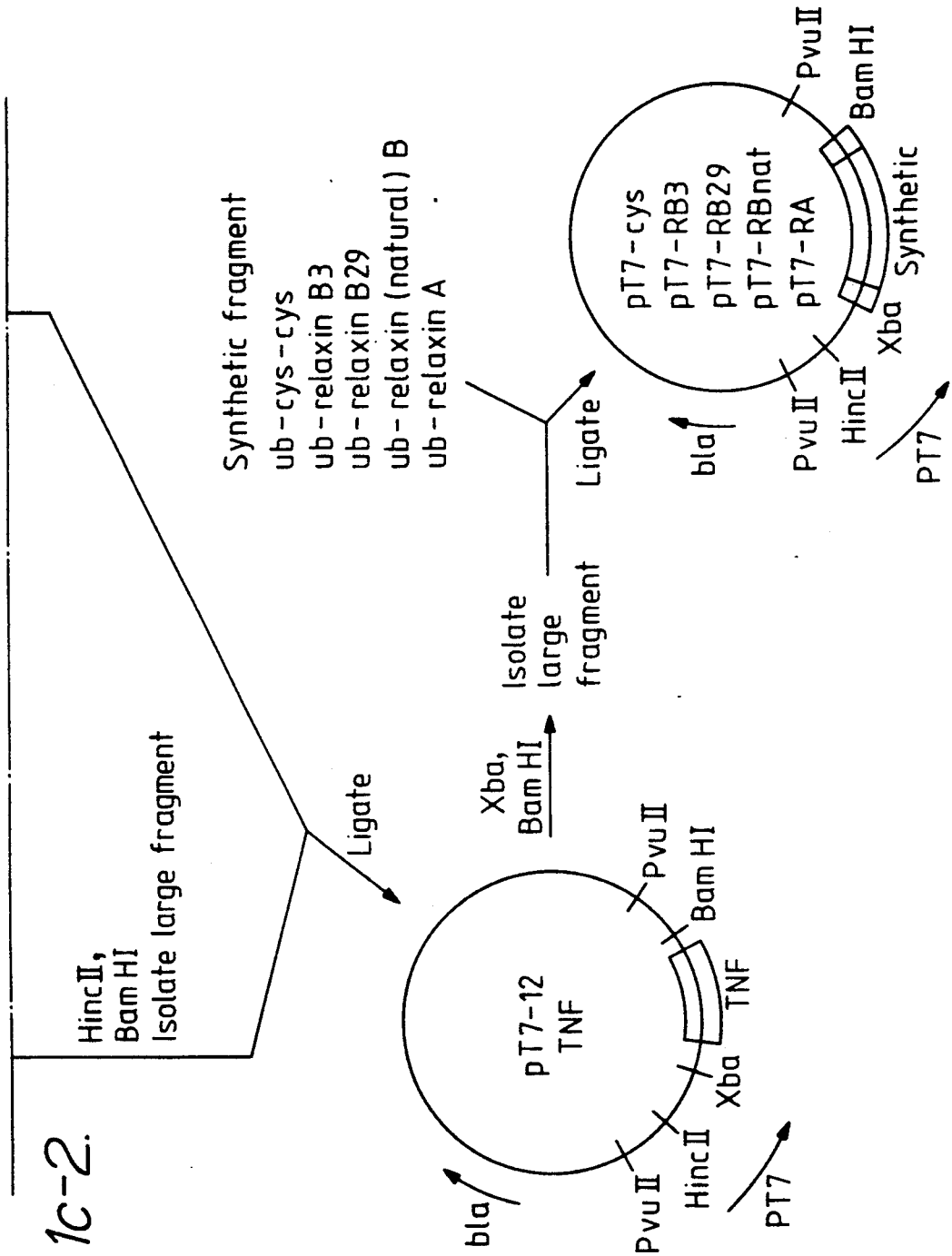
Figure 1D:
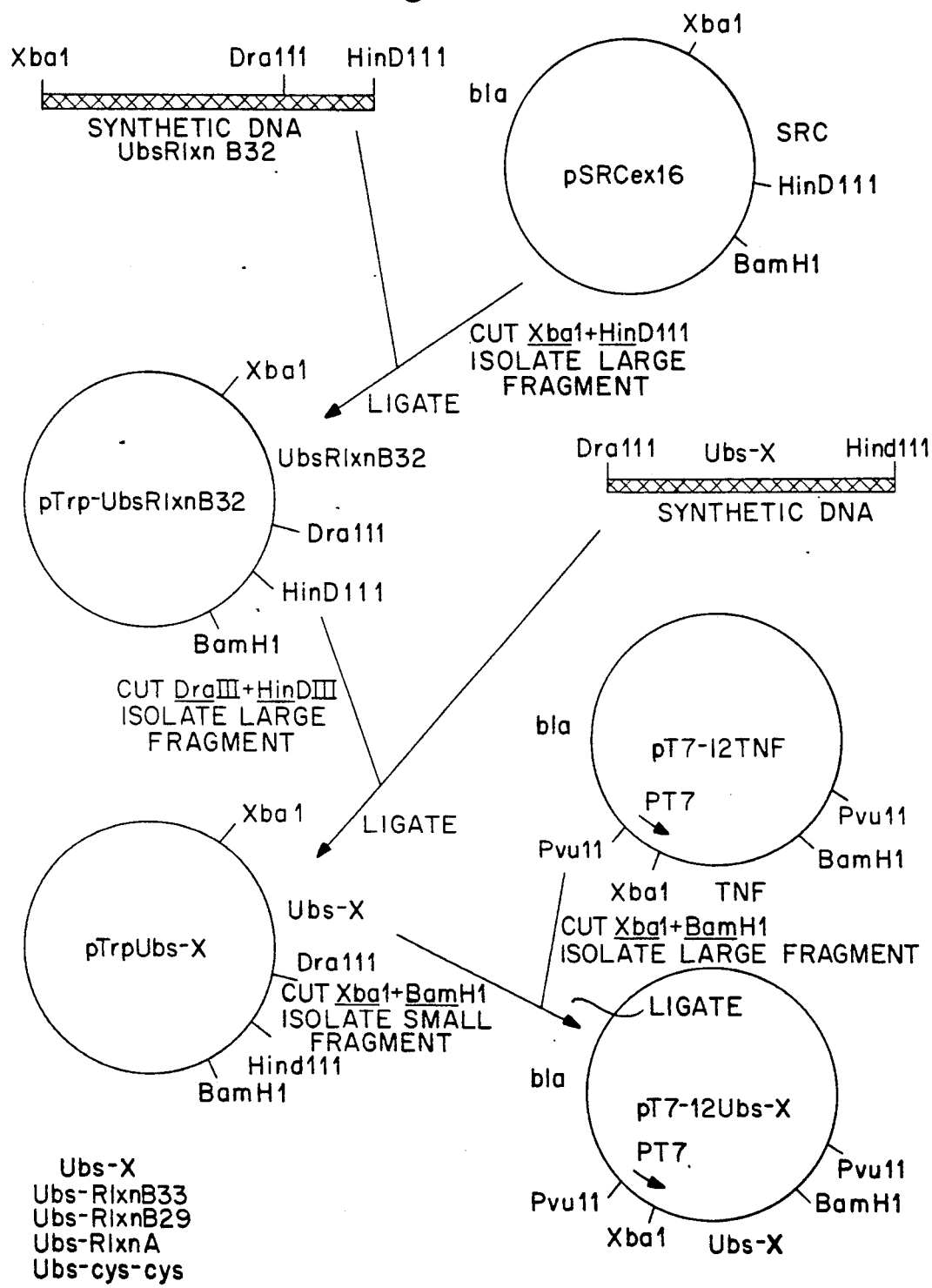
FIG. 1d depicts the construction of pT7-124bs-X.
Figure 2:
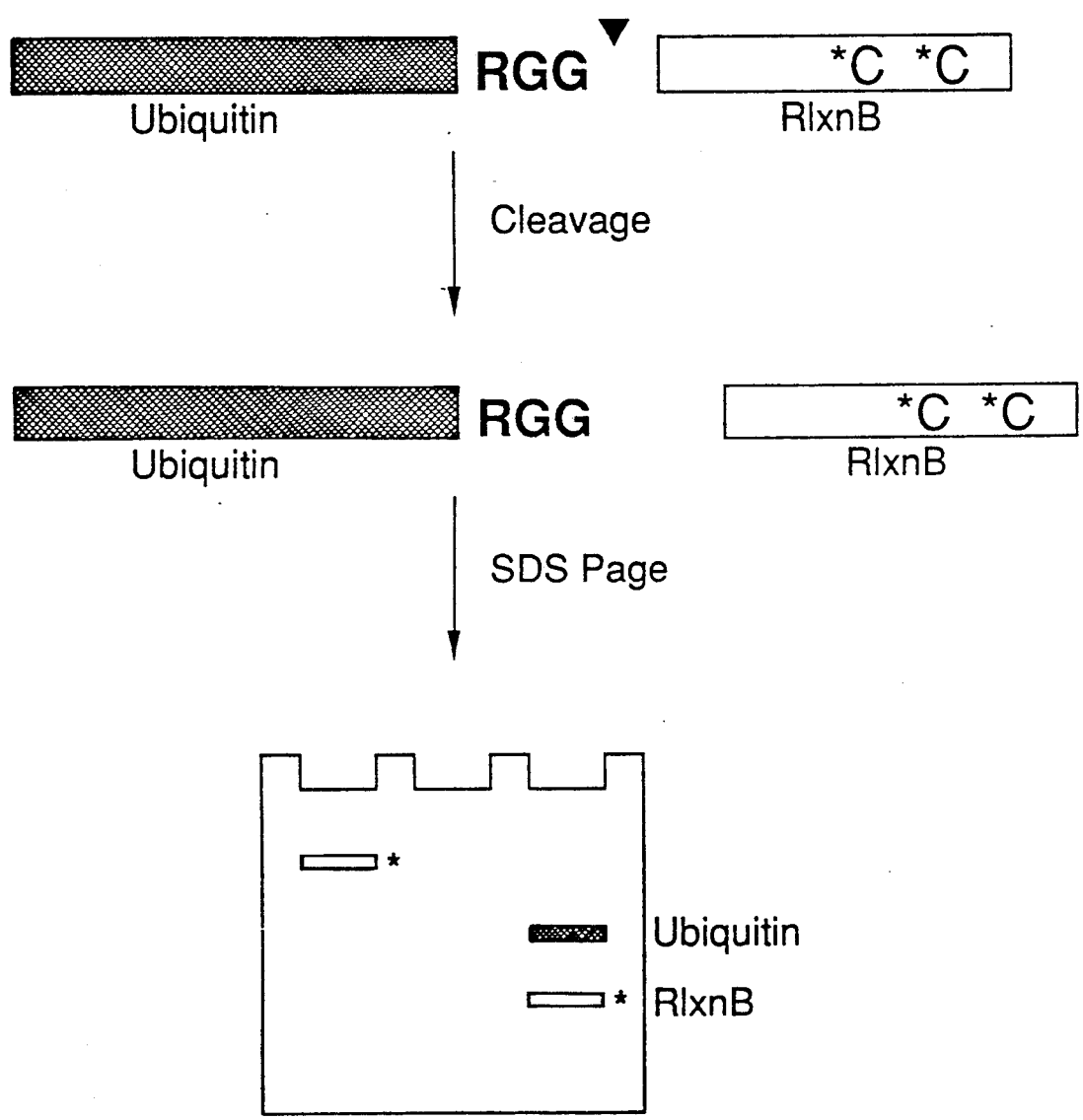

All assays were carried out in Eppendorf tubes with a final volume of 25 μl and incubation was at 37° C. for one hour. The reaction mix contained the following:

50 mM Tris-Cl (pH 7.5)
1 mM EDTA (pH 8.0)
10 mM dithiothreitol
1 μl S-35 Cys labeled ubiquitin-β chain relaxin substrate
2.5 μl ubiquitin hydrolase solution After incubation, the reaction was stopped by SDS sample buffer, loaded directly onto a 15% SDS gel, and monitored by electrophoresis to resolve the cleaved product from uncleaved substrates. Detection of various labeled protein species was done by drying the gel on a piece of Whatman No. 1 paper and exposing it to X-ray film overnight. A diagram depicting the principle of the assay is shown in FIG. 2.

Because the labeled substrate is obtained by in vivo labeling, it is limited in quantity and with undetermined specific activity. The best way to quantitate the amount of enzyme is to carry out the above reaction with serially diluted enzyme solutions with the same batch of substrate. The fold of dilution where the enzyme activity diminished can be used as an expression of the relative activity of a particular enzyme solution. The dilution buffer used for this purpose was the reaction cocktail with 50 μg/ml bovine serum albumin without enzyme and substrate.

2. Cleavage by cleaving ubiquitin-Cys-Cys

This assay is identical to the protein cleavage assay in principle except with a different substrate, ubiquitin-cys-cys. The cleaved products, ubiquitin and cys-cys, were separated by acid precipitation instead of SDS-PAGE because cys-cys is soluble in acid while the bigger ubiquitin is not.

All assays were carried out in Eppendorf tubes with a final volume of 25 μl, and incubation was at 37° C. for 20 minutes. The reaction mix contained the following:

50 mM Tris-Cl (pH 7.5)
1 mM EDTA (pH 8.0)
10 mM dithiothreitol
50 μg/ml bovine serum albumin
1 μl S-35 Cys labeled ubiquitin-Cys-Cys substrate
2.5 μl ubiquitin hydrolase solution After incubation, 20 μl of the reaction mixture was spotted onto a GF/C filter disc (2.1 cm) and immediately immersed in 10% (w/v) trichloroacetic acid (TCA) contained in a beaker over ice. Individual filter disc was labeled beforehand with Indian ink for identification after the washing procedures. The beaker was swirled occasionally during a five-minute period. The TCA solution was decanted and filters were further washed with 5% TCA solution. After another five minutes with occasional swirling, the TCA solution was again decanted. Filter discs were rinsed in 95% alcohol to remove TCA and dried under a heat lamp. Individual filter discs were placed into a counting vial, filled with 5 ml of counting fluid, and counted in a scintillation counter. Since the insoluble ubiquitin was retained on the filter disc, hydrolase activity was measured by the decrease of radioactivity retained by the filter disc.

Because the labeled substrate was obtained by in vivo labeling, it is limited in quantity and with undetermined specific activity. The specific activity of the hydrolase is also unknown at the present time. Therefore, the best way to quantitate the amount of the enzyme is to carry out the above reaction with serially diluted enzyme solutions with the same batch of substrate. The fold of dilution where the enzyme activity resulted in 60% retention of the original amount of radioactivity can be used as an expression of the relative activity of a particular enzyme solution. The dilution buffer used for this purpose is the reaction cocktail without enzyme substrate and enzyme itself.

II. Purification and Assay of Ubiquitin Hydrolase

All of the purification steps were conducted at room temperature except for the overnight dialysis and except for storage, which was at 4° C.

A. Fermentation

The yeast strain *Saccharomvces cerevisiae* is grown in a ten-liter fermenter at 30° C. in 2.6% yeast nitrogen base and 1% glucose to an $A_{660}$ of 3–4. Cells were then slowly fed with glucose until the $A_{660}$ reached 50–100.

B. Cell Homogenization

About one kg of the yeast strain fermentation paste is resuspended at 1 g/ml in Buffer A (50 mM Tris-Cl (pH8), 1 mM EDTA (pH8.0), 10% (v/v) glycerol, and 10 mM 2-mercaptoethanol). The resulting suspension is mixed with 0.25 g/ml of glass beads (Sigma G-8893, 106 microns and finer). The cell-glass beads suspension is blended in a Waring blender at top speed for several 2-3 minute-pulses for a total of ten minutes (care must be taken so that the temperature does not rise during this operation). The efficiency of cell breakage can be monitored by measuring protein concentration of the supernatant after a brief centrifugation of the suspension.

After homogenization, the suspension is centrifuged at 12,000 rpm in GSA rotor for about 30 minutes. Pellets are collected and resuspended in Buffer A (at the original 1 g/ml ratio) and are blended again for about five minutes (again, in two-minute pulses). The supernatant is collected after the centrifugation as before and combined with the first supernatant. The combined supernatant is further clarified by centrifugation at 18,000 rpm in ss-34 rotor for 30 minutes. The protein concentration at this stage is about 10 mg/ml or 20 mg/g of original wet yeast paste.

C. Ammonium Sulfate Fractionation

Ubiquitin hydrolase activity is recovered between 33% and 63% saturation of ammonium sulfate. Ammonium sulfate is added directly to the crude supernatant and the pH of the suspension is maintained by adding about 1 µl of 1 M Tris base per g of solid ammonium sulfate added. About half the protein is removed.

D. DEAE Chromatography

Protein precipitate after 63% ammonium sulfate saturation is collected by centrifuging the suspension from above in GSA rotor at 12,000 rpm for 30 minutes. Protein precipitate is resuspended in 350 ml of Buffer A and dialyzed against four liters of Buffer A with 80 mM NaCl (one buffer change in 72 hours). The dialyzed protein solution is loaded onto a DEAE Sephacel column (5×21 cm) equilibrated with Buffer A plus 80 mM NaCl at a flow rate of 400 ml per hour (the flow rate was slowed to about 80 ml per hour). The column is sequentially washed with Buffer A containing 80 mM NaCl. 170 mM NaCl 230 mM NaCl, and 300 mM NaGl. The buffer volume in each wash is about one liter. Almost all the activities eluted in the 300 mM NaCl wash and the column matrix, which is still heavily discolored at this point, are discarded. Active fractions are pooled (about 450 ml) and are subjected to the next column fractionation.

E. Phenyl-Sepharose Chromatography

Solid ammonium sulfate is added to the pooled DEAE fraction at the ratio of ten g per 100 ml of protein solution and loaded directly onto a phenyl-sepharose column (2.5×17 cm) equilibrated with Buffer A containing 10% (w/v) ammonium sulfate at a flow rate of about 50 ml per hour. The column is then washed with 100 ml each of Buffer A containing 10% (w/v) and then 5% ammonium sulfate. The enzyme is subsequently eluted with 350 ml of linear gradient composed of Buffer A with 5% ammonium sulfate and Buffer A. Active fractions, which are located in the early 20% of the linear gradient, are pooled (total volume is about 84 ml) and concentrated by ultrafiltration through an Amicon membrane. The concentrated enzyme solution (about 40 ml) is dialyzed overnight against one liter of Buffer B (50 mM Tris-Cl (pH8), 10% (v/v) glycerol. 10 mM 2-mercaptoethanol).

F. Hydroxylapatite Chromatography

The dialyzed enzyme solution is loaded onto a hydroxyapatite column (1.0×7 cm) equilibrated with Buffer B. The column is washed with 10 ml of Buffer B and then with 50 ml of a linear gradient between Buffer B and Buffer B containing 0.5 M ammonium sulfate. It is further washed with 10 ml each of Buffer B containing 0.5 M ammonium sulfate and then 1 M ammonium sulfate. Enzyme activities are located in the gradient and are then pooled (total volume is about 8 ml) and dialyzed overnight against Buffer A plus 0.1 M NaCl.

G. Rechromatography on DEAE Sephacryl

A DEAE Sephacryl column (0.7×7 cm) is loaded with dialyzed enzyme and the column is equilibrated with Buffer A containing 0.1 M NaCl and then washed with 5 ml of the same buffer. Enzyme activities are eluted with a 30-ml linear gradient between 0.1M NaCl and 1.0 M NaCl in Buffer A.

The activity is located around 0.3 M NaCl as expected and the overall yield at this point is at least 15% of the original activity present in the crude lysate.

H. SDS-PAGE

A reducing SDS-PAGE gel of the recovered activity is prepared and stained with silver stain. Upon visual inspection of the gel and comparison of the relative densities of the bands. it is found that the ubiquitin hydrolase obtained is about 70% pure based on the weight of the total protein in the composition, with a major protein species with molecular weight of about 30,000 daltons, comigrating with hydrolase activities throughout phenyl sepharose, hydroxyapatite and the last DEAE columns. This major band was confirmed by cloning of the gene to be the ubiquitin hydrolase protein.

I. HPLC and Sequencing

The recovered activity from the DEAE column was placed on a 4000 angstrom wide-pore column (100 mm ×2mm in diameter) from Synchrom, Inc. in a Hewlett Packard C4 RP-HPLC 190M equipped with a 1040 diode array detector. A linear gradient was used of 100% solution A to 60% solution B in 60 minutes, wherein solution A is 0.1% trifluoroacetic acid (TFA) in water and solution B is 0.07% TFA in 1-propanol. The flow rate was 200 µl per minute at room temperature and the peaks were monitored at 214 and 280 nm. All the peaks with 214 nm absorption were collected in the buffer used for the particular assay of the hydrolase activity.

There was one positive assay from the peaks collected that had a 30 kDa molecular weight on a reducing SDS-PAGE gel. One fraction from the DEAE column that was 90% enriched in the 30 kDa protein was digested by adding about 5% Lycine C (Wako) to the fraction in its elution buffer. The digestion was carried out for 24 hours at 37° C. The peptides were separated on the C4-HPLC column mentioned above using the same conditions as described above. The separated peptides were sequenced on an Applied Biosystems 470A gas phase sequencer using Edman degradation. The following amino acid sequences were obtained:

1. SDPTATDLIEQELVRVRVA
2. ENVQTFSTGQSEAPEATADTNLHYI
3. NEWAYFDIY
4. NRFDDVTTQ.

III. Cloning and Expression of the Hydrolase Gene

A synthetic DNA probe was synthesized on a DNA synthesizer using the method of Froehler et al., supra. This probe (Probe 1, 53 mer) had the following sequence:

```
5'-GACCCAACTGGTACTGACTTGATC-
GAACAAGAATTGGTTAGAGT-
TAGAGTTGG-3'
```

Total genomic DNA was isolated from a yeast strain S17990 (αtro5 his4 ade6 ga12) of *Saccharomyces cerevisiae* by the method of Smith et al., *Method Enzymol.*, 12: 538–541 (1967). 370 µg of yeast DNA was partially digested with 2.5 units of Sau3AI (New England Biolabs) in 2 ml of reaction mixture. Aliquots were removed at 10, 20, and 30 min., chilled, and inactivated with 20 mM EDTA. The pooled, phenol-extracted DNA was fractionated by centrifugation in 10–50% sucrose gradients in 1 M NaCl, 20 mM Tris-HCl (pH 8.0), and 10 mM EDTA. The Sau3AI 15-kb fragments (determined by agarose gel electrophoresis) were isolated and ligated into bacteriophage λ Charon 30 cut with BamHI-isolated arms (Maniatis et al., supra). The DNA was packaged in vitro using Gigapack (Strategene).

The resultant phage were then plated on an *E. coli* DP50 strain (commercially available). Ten-thousand plaques were lifted onto non-sterilized nitrocellulose filters (Schleicher and Schuell, BA85, 132 nm diameter). The filters were denatured by contact with a solution of 0.5M NaOH, 1 M NaCl. Then they were renatured in a solution of Tris, pH 7.5, 3M NaCl and washed in 2 ×SSC. After renaturation, the filters were treated at 42° C. for five minutes in a prehybridization buffer consisting of 5 ×SSPE (20 ×SSPE is prepared by dissolving 174 g of NaCl, 27.6 g of $NaH_2PO_4.H_2O$, and 7.4 g of EDTA in 800 ml of water with pH adjusted to 7.4 and volume adjusted to 1 liter), 5 ×Denhardt's solution (1×Denhart's solution=0.1% Ficoll, 0.1% polyvinylpyrrolidone, 0.1% BSA), 0.1 mM ATP, 0.2 μg/ml sonicated salmon sperm DNA, 20% formamide, and 0.1% SDS. Then Probe 1, labeled at its 5' end with radioactive phosphorus by known techniques, was added to the prehybridization mixture at a concentration of $2\times10^6$ cpm per ml.

The filters were incubated with probe 1 for one hour at 42° C. Then the filters were removed from the probe solution and washed three times in 2 ×SSC plus 0.1% SDS at 37° C. for 15 min. The filters were exposed to x-ray film for three hours at −70° C. Positive plaques were chosen and grown in liquid media for DNA.

After growth of the phage, the DNA was extracted and cleaved with several restriction enzymes. The resulting fragments were placed on nitrocellulose filters and treated with prehybridization buffer and Probe I as described above. The probe was found to hybridize to a 1.4 kb SalI to BamHI fragment on phage λ7. This fragment was isolated from λ 7.

M13mp18 and M13mp19 bacteriophages, available from New England Biolabs, were cleaved with SalI and BamHI and the large fragment was isolated. The fragment from λ7 was ligated with the large fragments from M13mp18 and M13mp19 such that the fragment from λ7 was under the control of the lac promoter. The fragment in the M13mp18 bacteriophage was sequenced by the dideoxy-chain termination method of Sanger et al, supra, from the SalI site to the Bam site, using a synthetic phage-specific primer. Samples were separated by electrophoresis on 5% polyacrylamide/8M urea "thin" gels. Gels were dried onto Whatman 3MM paper and exposed to Kodak x-ray film for varying lengths of time.

Figure 4:
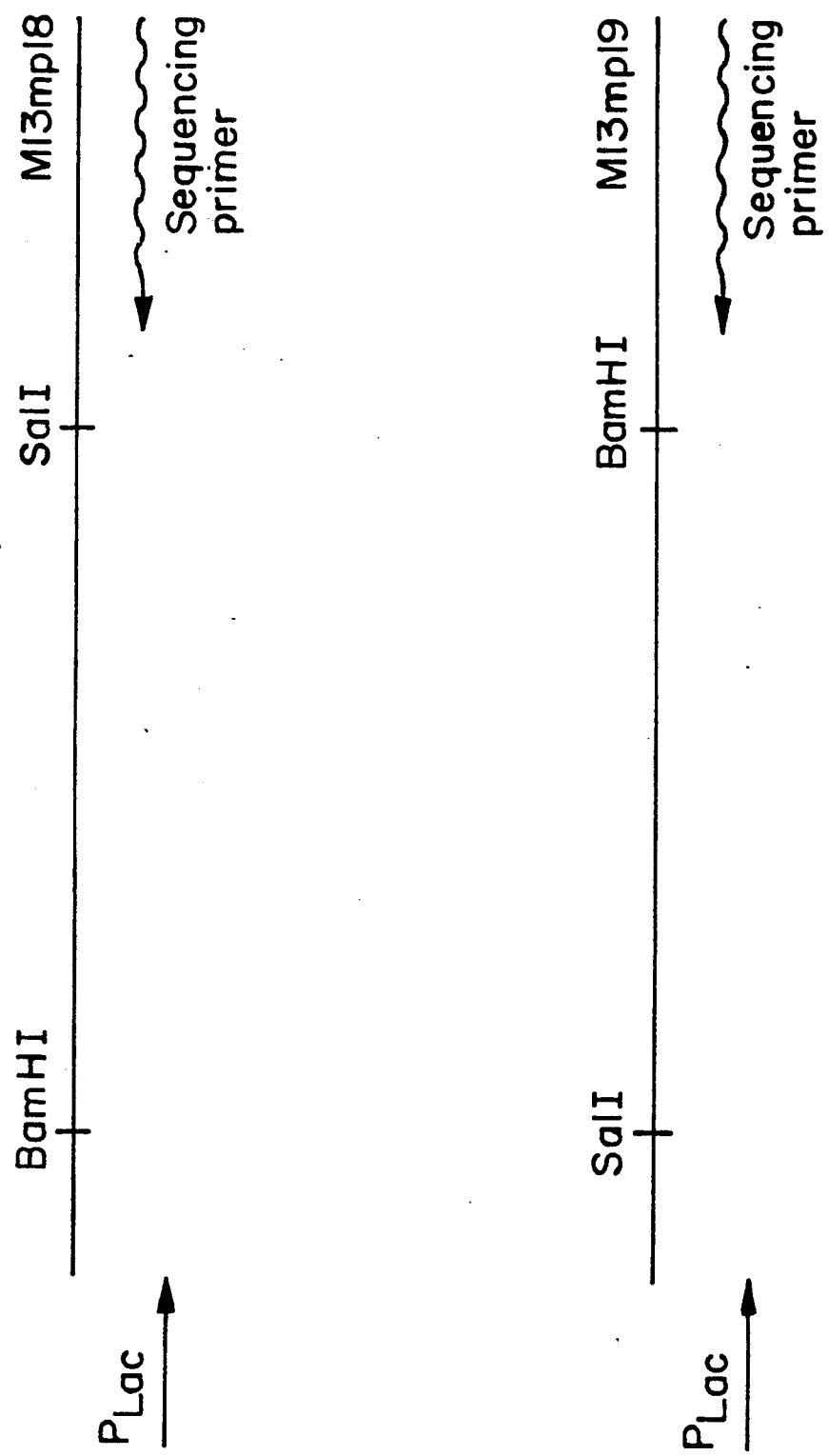

FIG. 3 shows the nucleotide sequence determined for the fragment from the SalI end to within about 300 bases of the BamHI end, as well as the imputed amino acid sequence and the positions of various restriction sites and the position of probes 1 and 2. FIG. 4 shows the direction of the sequencing.

The M13mp19 bacteriophage containing the hydrolase insert was grown in *E. coli* strain SR101 (commercially available) using as the culture media LB Broth. The production of protein was induced by adding 1 mM of IPTG to the culture medium.

Lysis of the S101 cells was performed using the lysate procedure described in the protein assay section herein for preparing the labeled protein substrate for ubiquitin hydrolase from K5772.

The cell lysate was clarified by centrifugation and then assayed for activity by the fusion polypeptide assay described above. The assay showed detectable ubiquitin hydrolase activity by both assays, indicating that the DNA sequences cloned encoded hydrolase protein and were induced by IPTG.

EXAMPLE II

DNA fragments encoding yeast ubiquitin were synthesized chemically on a DNA synthesizer using methoxyphosphoramidites. The yeast ubiquitin gene was synthesized connected to the gene coding for human (H2) relaxin B chain of 32 amino acids, with the sequence shown in FIG. 1b, to human (H2) relaxin A chain of 24 amino acids, to prorelaxin, and to the human (H2) relaxin B chain as it is found naturally, with the sequence shown in FIG. 1a. XbaI and BamHI sites were added to the ends of each DNA segment. The prorelaxin construct is described in European Pat. Pub. 260,149 published Mar. 16, 1988. The DNA sequence for A-chain relaxin is provided in EP Pub. No. 112,149, supra. The disclosures of both of these patent publications are incorporated by reference herein.

The synthetic genes were separately cloned into the large fragment after XbaI and BamHI digestion of the plasmid trp 207-1*tetxap, described in detail in European Pat. Pub. 260,149. The ubiquitin-fusion polypeptide gene was ligated such that the ubiquitin fusion polypeptide was under the control of the trp promoter of the trp 207-1*tetxap plasmid. *E. coli* strain MM294 (commercially available) was transformed with the resulting plasmids and the synthesis of the fusion proteins was induced by adding indoleacrylic acid to the culture medium. SDS-PAGE analysis using silver staining under reducing conditions revealed a prominent protein band. Upon Western blotting analysis this band reacted with an antibody directed against the appropriate relaxin moiety. The band was found to correspond to the correct molecular weight in each instance.

The culture of each transformant is then fermented, harvested, and run through an affinity chromatography column on which are immobilized anti-ubiquitin monoclonal antibodies. The material bound to the column is eluted and run through a column having the ubiquitin hydrolase purified as described above adsorbed thereto. The eluent from the column is passed through the affinity chromatography column on which are immobilized the anti-ubiquitin monoclonal antibodies. The first fractions containing separately the various relaxin polypeptides are obtained and pooled, free from the cleaved ubiquitin, the ubiquitin fusion polypeptide, and all cellular debris.

We claim:

1. A composition comprising yeast ubiquitin hydrolase in a purity of at least 70% homogeneity based on the weight of the total protein in the composition, which hydrolase hydrolyzes a ubiquitin-polypeptide conjugate at the amide bond linking the ubiquitin and polypeptide, thereby yielding intact polypeptide with an unconjugated, mature N-terminus.

2. The composition of claim 1 wherein the hydrolase is present in a buffer.

* * * * *